United States Patent
Zhang et al.

(10) Patent No.: US 10,988,274 B2
(45) Date of Patent: Apr. 27, 2021

(54) PACKAGING FOR ADHESIVE COMPOSITIONS

(71) Applicant: ADHEZION BIOMEDICAL, LLC, Wyomissing, PA (US)

(72) Inventors: Sheng Zhang, Hickory, NC (US); Rafael Ruiz, Sr., Hudson, NC (US); Amanda Guido, Granite Falls, NC (US)

(73) Assignee: ADHEZION BIOMEDICAL, LLC, Wyomissing, PA (US)

( * ) Notice: Subject to any disclaimer, the term of this patent is extended or adjusted under 35 U.S.C. 154(b) by 658 days.

(21) Appl. No.: 15/426,734

(22) Filed: Feb. 7, 2017

(65) Prior Publication Data
US 2018/0222618 A1 Aug. 9, 2018

(51) Int. Cl.
*B32B 1/02* (2006.01)
*A61J 1/16* (2006.01)
(Continued)

(52) U.S. Cl.
CPC .............. *B65B 55/16* (2013.01); *A61B 50/30* (2016.02); *A61J 1/16* (2013.01); *A61L 2/0082* (2013.01); *A61L 2/081* (2013.01); *A61L 2/082* (2013.01); *A61L 2/087* (2013.01); *A61L 2/12* (2013.01); *A61L 2/206* (2013.01); *A61L 24/04* (2013.01); *A61L 24/12* (2013.01); *B32B 1/02* (2013.01); *B32B 1/08* (2013.01); *B65B 3/003* (2013.01); *B65B 55/10* (2013.01); *B65D 1/09* (2013.01); *B65D 65/38* (2013.01); *B65D 75/04* (2013.01); *B65D 75/26* (2013.01); *B65D 75/38* (2013.01); *B65D 77/04* (2013.01); *B65D 77/20* (2013.01); *C08F 22/32* (2013.01); *C09J 4/00* (2013.01); *A61B 17/00491* (2013.01);
(Continued)

(58) Field of Classification Search
CPC .. A61L 24/04; A61L 24/12; A61J 1/16; B32B 1/02; B32B 1/08
See application file for complete search history.

(56) References Cited

U.S. PATENT DOCUMENTS 2,721,858 A  10/1955 Joyner et al.
3,254,111 A   5/1966 Hawkins et al.
(Continued)

FOREIGN PATENT DOCUMENTS

DE   69921672    3/2005
EP    1864909   12/2007

OTHER PUBLICATIONS

International Search Report by the European Patent Office dated Apr. 25, 2018 for the International Application No. PCT/US2018/015893.

*Primary Examiner* — Walter Aughenbaugh
(74) *Attorney, Agent, or Firm* — Stradley Ronon Stevens & Young, LLP

(57) ABSTRACT

A package system suitable for sterilizing cyanoacrylate compositions and providing the sterile cyanoacrylate compositions a shelf life of at least 24 months, wherein the package system comprises: an ampoule comprising a chamber comprising a cyanoacrylate monomer, wherein the chamber is defined by an opening and sidewalls, wherein the ampoule comprises a material comprising a cyclic olefin copolymer; a multilayer foil seal sealing the opening of the ampoule; and a secondary package housing the ampoule.

8 Claims, 1 Drawing Sheet

(51) Int. Cl.

| | | |
|---|---|---|
| *B65B 55/16* | (2006.01) | |
| *C09J 4/00* | (2006.01) | |
| *C08F 22/32* | (2006.01) | |
| *A61L 2/20* | (2006.01) | |
| *A61L 2/08* | (2006.01) | |
| *A61L 2/12* | (2006.01) | |
| *B65D 1/09* | (2006.01) | |
| *B65B 55/10* | (2006.01) | |
| *B65B 3/00* | (2006.01) | |
| *B65D 77/20* | (2006.01) | |
| *B65D 77/04* | (2006.01) | |
| *B65D 65/38* | (2006.01) | |
| *B65D 75/38* | (2006.01) | |
| *B65D 75/04* | (2006.01) | |
| *A61L 2/00* | (2006.01) | |
| *B65D 75/26* | (2006.01) | |
| *A61B 50/30* | (2016.01) | |
| *B32B 1/08* | (2006.01) | |
| *A61L 24/04* | (2006.01) | |
| *A61L 24/12* | (2006.01) | |
| *A61B 17/00* | (2006.01) | |

(52) U.S. Cl.
CPC ... *A61B 2050/314* (2016.02); *A61B 2050/316* (2016.02); *A61L 2202/23* (2013.01)

(56) References Cited

U.S. PATENT DOCUMENTS

| | | |
|---|---|---|
| 3,523,628 A | 8/1970 | Colvin et al. |
| 4,364,876 A | 12/1982 | Kimura et al. |
| 4,685,591 A | 8/1987 | Schaefer et al. |
| 4,698,247 A | 10/1987 | Murray et al. |
| 4,777,085 A | 10/1988 | Murray, Jr. et al. |
| 5,016,784 A | 5/1991 | Batson |
| 5,480,935 A | 1/1996 | Greff et al. |
| 5,730,994 A | 3/1998 | Askill et al. |
| 5,807,563 A | 9/1998 | Askill et al. |
| 5,881,536 A * | 3/1999 | Muller-Wille .......... B65B 55/02 53/425 |
| 5,928,611 A | 7/1999 | Leung |
| 6,248,800 B1 | 6/2001 | Greff et al. |
| 6,328,910 B1 * | 12/2001 | Askill .................... A61B 5/489 252/299.01 |
| 6,579,469 B1 | 6/2003 | Nicholson et al. |
| 6,620,846 B1 | 9/2003 | Jonn et al. |
| 6,951,898 B2 * | 10/2005 | Hammond ............. C08K 5/103 524/291 |
| 7,179,521 B2 | 2/2007 | Arthurs et al. |
| 7,384,674 B2 * | 6/2008 | Andersson .............. B32B 15/08 428/36.7 |
| 8,198,344 B2 | 6/2012 | Zhang et al. |
| 8,293,838 B2 | 10/2012 | Zhang et al. |
| 9,272,095 B2 | 3/2016 | Felts et al. |
| 2005/0047846 A1 | 3/2005 | Narang et al. |
| 2005/0197421 A1 | 9/2005 | Loomis |
| 2006/0062687 A1 | 3/2006 | Morales |
| 2006/0186005 A1 * | 8/2006 | Ebnesajjad ........... B65B 25/008 206/363 |
| 2007/0078207 A1 | 4/2007 | Jonn et al. |
| 2008/0021139 A1 | 1/2008 | Blacklock et al. |
| 2008/0241249 A1 | 10/2008 | Quintero et al. |
| 2009/0208685 A1 | 8/2009 | Rivers et al. |
| 2010/0189942 A1 | 7/2010 | Tamura et al. |
| 2010/0269749 A1 | 10/2010 | Badejo et al. |
| 2010/0330027 A1 | 12/2010 | Liu |
| 2013/0108352 A1 | 5/2013 | Ruiz, Sr. et al. |
| 2014/0311941 A1 | 10/2014 | Zhang et al. |
| 2014/0370278 A1 | 12/2014 | Hausmann et al. |
| 2016/0361232 A1 * | 12/2016 | Chou ....................... A61J 1/16 |

* cited by examiner

PACKAGING FOR ADHESIVE COMPOSITIONS

BACKGROUND OF THE INVENTION

Field of the Invention

The invention relates to package elements for storing and sterilizing adhesive compositions suitable for various irradiation sterilization methods. In particular, the invention relates to a suitable packaging material and system for storing and sterilizing adhesive compositions via irradiation techniques, which provide an extended shelf life of at least two years.

Description of the Prior Art

Various publications, including patents, published applications, technical articles and scholarly articles are cited throughout the specification. Each of these cited publications is incorporated by reference herein, in its entirety and for all purposes.

Cyanoacrylate adhesives are liquid monomers that polymerize on contact with tissue surfaces in an exothermic reaction creating a strong yet flexible film. This polymer film is generally formed rapidly. Liquid cyanoacrylate compositions have found new application as medical adhesives for closing wounds and incisions, especially in cases where suturing does not provide satisfactory results because of its unique ability to bond living tissue and their long-term bond strength.

Cyanoacrylate adhesives need to be sterilized to be used for a medical application. The sterilization of cyanoacrylate compositions can be accomplished by common techniques such as heat sterilization, ethylene oxide sterilization, microwave sterilization, UV light sterilization, gamma irradiation and electron beam sterilization. However, limitations occur when different sterilization methods are used to sterilize cyanoacrylate compositions. The toxic and explosive nature as well as the ineffective sterilization of ETO prevents a broader application of ETO on the sterilization of cyanoacrylate compositions. It is well-known that irradiation sterilization can have a drastic effect on the stability and performance of cyanoacrylate compositions, as disclosed in U.S. Pat. Appl. Pub. No. 2008/0021139 to Blacklock et al., U.S. Pat. Appl. Pub. No. 2005/0197421 to Loomis, and U.S. Pat. No. 6,248,800 to Greff et al. in that high doses of aggressively penetrating gamma or E-beam irradiation will cause changes in the cyanoacrylate adhesive compositions and attempts to minimize these changes require the addition of very high levels of inhibitors. Such high levels of inhibitors increase the toxicity of the mixture and increase the toxic by-products formed upon gamma irradiation. The use of high doses of toxic gamma irradiation to effect sterilization also raises safety concerns for workers who are exposed long term to this radiation. High temperatures required for the dry heat sterilization processes could cause premature polymerization of the cyanoacrylate monomers.

In addition, application time needs to be short for the adhesive to be used in a medical/surgical setting. However, some cyanoacrylate monomers with long alkyl chains or with high viscosity require a relatively longer time to polymerize. To address this problem, a polymerization accelerator is typically incorporated into cyanoacrylate compositions for improving the curing speed of the adhesives. But the adverse effect of sterilization on cyanoacrylate compositions would be exacerbated in the presence of polymerization accelerators. In order to overcome the potential challenge induced by the polymerization accelerator during the sterilization process, the prior art has disclosed different approaches such as the separation of the polymerization accelerators from the cyanoacrylate monomer during the sterilization process. U.S. Pat. Appl. Pub. Nos. 2005/0047846 to Narang et al. and 2007/0078207 to Jonn et al. and U.S. Pat. No. 6,579,469 to Nicholson et al. reveal that the polymerization accelerators are applied to the applicator tip, or to be coated on an interior surface of the applicator body, or on an exterior surface of an ampoule or other container disposed within the applicator body. It was also pointed out that a non-contacting relationship between the porous applicator tip which contains the polymerization accelerator and the adhesive monomer should be maintained prior to the sterilization and dispensing. Similar statements are also seen in U.S. Pat. Appl. Pub. Nos. 2010/0330027 to Liu, 2010/0269749 to Badejo et al., and 2008/0241249 to Quintero et al. and U.S. Pat. Nos. 6,620,846 to Jonn et al. and 5,928,611 to Leung disclose an applicator tip having a polymerization or cross-linking initiator or accelerator disposed on or in a solid support in the applicator tip, wherein said cyanoacrylate monomer is located in said container body in a non-contacting relationship with said tip prior to dispensing said material.

Nonetheless, incorporation of polymerization accelerators into the applicator tip is a complicated process since the polymerization accelerator has to either be applied as a solid coating onto the applicator tip by vapor deposition such as by sputtering, or be incorporated into the applicator tip by mixing the accelerator with the applicator tip material prior to molding. It is difficult to uniformly distribute the polymerization accelerator onto the applicator tip via such processes. It is also hard to control the amount of accelerator dissolved into the adhesive composition passing through the applicator tip. It can lead to clogging of the applicator if too much accelerator is incorporated resulting in an extremely fast curing. On the other hand, the accelerating effect may not be achieved if too little accelerator is incorporated when the adhesive flows through the applicator tip.

It would thus be desirable to design a package system in which cyanoacrylate adhesive composition can be sterilized in the presence of miscible polymerization accelerator without having to separate the polymerization accelerator from the cyanoacrylate adhesive composition. It would also be desirable that such cyanoacrylate compositions containing polymerization accelerator upon sterilization in said delivery system can provide an extended shelf life.

Many packaging materials for cyanoacrylate compositions have been disclosed in the prior art. For example, U.S. Pat. No. 3,523,628 to Colvin et al. discloses a container for non-sterile cyanoacrylate compositions to afford the long shelf stability of cyanoacrylate adhesives by minimizing the premature polymerization of the materials. U.S. Pat. No. 4,685,591 to Schaefer et al. and U.S. Pat. Nos. 4,698,247 and 4,777,085 to Murray et al. disclose a multiple layer packaging sheet material which can be formed into closed and sealed packages suitable for holding cyanoacrylate compositions. Due to their barrier properties, fluoropolymers are also used as the packaging materials for moisture sensitive adhesives such as cyanoacrylate compositions. U.S. Pat. No. 5,016,784 to Batson discloses a plunger-type syringe for moisture-sensitive adhesives. The syringe consists of a layer of hydrocarbon grease to separate the face of the plunger and the cyanoacrylate compositions. Most of the packaging materials disclosed in prior arts are related to the packaging of non-sterile cyanoacrylate compositions, which are generally used as industrial adhesives.

Cyclic olefin copolymers (COC) are known to be used as packaging component. For example, U.S. Pat. Appl. No. 2014/0370278 by Hausmann et al. discloses a multilayer film where there is a puncture resistant layer with one cyclic olefin copolymer layer and one ionomer or polyolefin layer. U.S. Pat. Appl. No. 2010/0189942 by Tamura et al. teaches a multi-layer resin film or blister packaging material in which different embodiments consist of at least one layer of cyclic olefin polymer. U.S. Pat. Appl. No. 2009/0208685 by Rivers et al. discloses subject matter that is directed to packaging films including semi-crystalline cyclic olefin copolymers, amorphous cyclic olefin copolymers, and/or cyclic olefin polymers present in the sealant layer and/or in the layer adjacent to the sealant layer such that the film exhibits decreased scalping of essential oils, flavor compounds, antibacterial additives, antifungal additives, and the like from products packaged using the disclosed films. U.S. Pat. No. 9,272,095 to Felts et al. discloses a vessel wall coated with various layers of COC and other materials to provide various barriers. U.S. Pat. No. 7,179,521 to Arthurs et al. discloses a multilayer shrink film containing one or more COC inner layer(s) where the COC for this invention must be limited to a single site catalyzed COC. However, the use of COC for packaging and sterilizing moisture-sensitive cyanoacrylate compositions has never been investigated in the prior art as far as we know.

The present invention thus discloses a storage and delivery system for cyanoacrylate compositions that is compatible with the different sterilization methods. It is also the intention of the present invention to develop a suitable delivery system in which cyanoacrylate compositions comprising a polymerization accelerator can be readily sterilized and provide an extended shelf life of at least two years.

SUMMARY OF THE INVENTION

The invention provides for suitable packages for sterilizing cyanoacrylate compositions via irradiation methods, such as E-beam, Gamma, or X-ray sterilization. The package comprises a primary package and a secondary overpack. The primary package may consist of a plastic ampoule and a multi-layer foil seal or a heat-seal container/pouch. The secondary overpack may consist of a front wrapper and a back wrapper. The primary package may be constructed with gas/moisture resistible materials. The plastic ampoule and the multi-layer foil seal may be heat-sealed together to form a container at elevated temperature and pressure to ensure a leak-free environment. Part of or the entire secondary overpack may be constructed with a gas-permeable material so that vapor and/or gas can penetrate the secondary overpack. The package body, as the delivery system of the stable cyanoacrylate compositions, may be constructed as bottles, applicators, vials, syringes, ampoules, or the like.

According to one embodiment, the invention provides for a method for sterilizing and storing cyanoacrylate compositions in the absence or presence of a polymerization accelerator. The method for sterilizing cyanoacrylate compositions in a package system includes (1) preparing cyanoacrylate monomer(s) with a purity of about 97-99% by weight; (2) stabilizing cyanoacrylate compositions with free radical and anionic polymerization inhibitors, filtering cyanoacrylate composition and dissolving polymerization accelerator in the cyanoacrylate compositions; (3) filling and sealing the cyanoacrylate compositions into a primary package; (4) sterilizing the cyanoacrylate compositions in the primary package system via an irradiation method; (5) assembling the primary package into an applicator with an applicator tip and packing into a secondary overpack; and (6) sterilizing the whole package system via a chemical sterilization.

The packages for storing the cyanoacrylate adhesive compositions may include a small amount of stabilizers. Large amounts of stabilizers can increase the toxicity of the cyanocrylate adhesive compositions. The cyanocrylate compositions, as packaged, can be effectively sterilized via E-beam, Gamma, or X-ray irradiation in the presence of smaller amounts of the anionic stabilizers, such as 80 ppm or less. The barrier property of the packages are suitable for the irradiation sterilization methods, which provides the sterility and long term stability of the cyanoacrylate adhesive compositions even in the presence of a small amount of stabilizer(s).

According to one embodiment, the invention provides a package system that may be sterilized by the combination of irradiation and other sterilization methods. The package system includes a stable cyanoacrylate composition having a viscosity (e.g., ranging from about 1-500 centipoise or cPs), an ampoule/container, and a secondary overpack. The ampoule contains the stable cyanoacrylate composition sealed with a multi-layer foil seal. The ampoule is made from an oxygen and/or moisture impermeable material. The ampoule is sterilized by irradiation while maintaining the viscosity of the stable cyanoacrylate composition such that a change in the viscosity is no more than 200 cPs. The secondary overpack includes a gas permeable back wrapper housing the ampoule containing the stable cyanoacrylate composition. The secondary overpack is sterilized by chemical sterilization while maintaining the viscosity of the stable cyanoacrylate composition such that a change in the viscosity is no more than 100 cPs. Thus, the package system provides a sterilized and stable cyanoacrylate composition with a shelf life of at least 12 months, preferably at least 24 months.

One advantage of the invention is the selection of suitable package systems for cyanoacrylate adhesive compositions, which are compatible with the irradiation methods such as E-beam, Gamma, or X-ray sterilization to effectively sterilize the cyanoacrylate monomers inside. The components of the package are stable upon irradiation. The packages provide a desired barrier to moisture so that premature polymerization of the sterilized cyanoacrylate monomer can be inhibited and prevented.

The irradiation methods were found to have a negligible effect on the performance of the cyanoacrylate adhesive compositions stored in the packages described herein. It was found that viscosity and set time of different cyanoacrylate compositions may only vary slightly upon sterilization methods, indicating that irradiation techniques such as E-beam, Gamma, or X-ray sterilization are compatible with the packaging to provide sterile and stable cyanoacrylate monomer compositions.

The invention provides for a suitable package for storing and sterilizing cyanoacrylate adhesive compositions wrapped with a secondary overpack. The secondary overpack may consist of a front wrapper and a back wrapper. The secondary overpack materials are preferably compatible with radiation or ETO sterilization methods.

The cyanoacrylate compositions are preferably highly pure, for example, on the order of about 98% purity. The high purity of cyanoacrylate monomer may be obtained, for example, by multiple distillations under high vacuum and high temperature. The cyanoacrylate compositions may contain free radical and anionic stabilizers. A trace amount of polymerization accelerator may be dissolved in the cyanoacrylate compositions before storing in the package systems.

The package system may consist of a plastic container and a multi-layer foil seal. The plastic container may be heat-sealed by the multi-layer foil seal after the adhesive is filled into the container. The temperature used to seal the plastic ampoule and the seal foil may be in the range of about 100° C. to about 250° C., preferably about 120° C. to about 250° C., and more preferably about 120° C. to about 220° C. The pressure used to seal the plastic container and the multi-layer seal foil may be in the range of about 1 bar to about 50 bar, preferably about 1 bar to about 40 bar, more preferably about 1 bar to about 25 bar, and most preferably about 1 bar to about 15 bar.

The irradiation methods were found to have a negligible effect on the performance of the cyanoacrylate adhesive compositions stored in the packages described herein. It was found that viscosity and set time of different cyanoacrylate compositions may only vary slightly upon sterilization methods, indicating that irradiation techniques such as E-beam, Gamma, or X-ray sterilization are compatible with the packaging to provide sterile and stable cyanoacrylate monomer compositions.

The package for storing and sterilizing the cyanoacrylate adhesive compositions via irradiation methods help to provide for an extended shelf life of the cyanoacrylate adhesive compositions. For example, the shelf life may be on the order of 12 months or more, preferably at least 24 months. The shelf life stability of the cyanoacrylate compositions with small amounts of stabilizers in the packaging system, as evaluated by the accelerated aging shelf life study (e.g., accelerated aging tests at 55° C. for 85 days and at 80° C. for 13 days) as well as the real time shelf life study, confirms an extended shelf life of at least 2 years of the cyanoacrylate adhesive compositions in the package after the irradiation sterilization.

DETAILED DESCRIPTION OF THE PREFERRED EMBODIMENTS

The terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." Unless specified otherwise, all values provided herein include up to and including the endpoints given, and the values of the constituents or components of the compositions are expressed in weight percent or % by weight of each ingredient in the composition.

Figure 1:
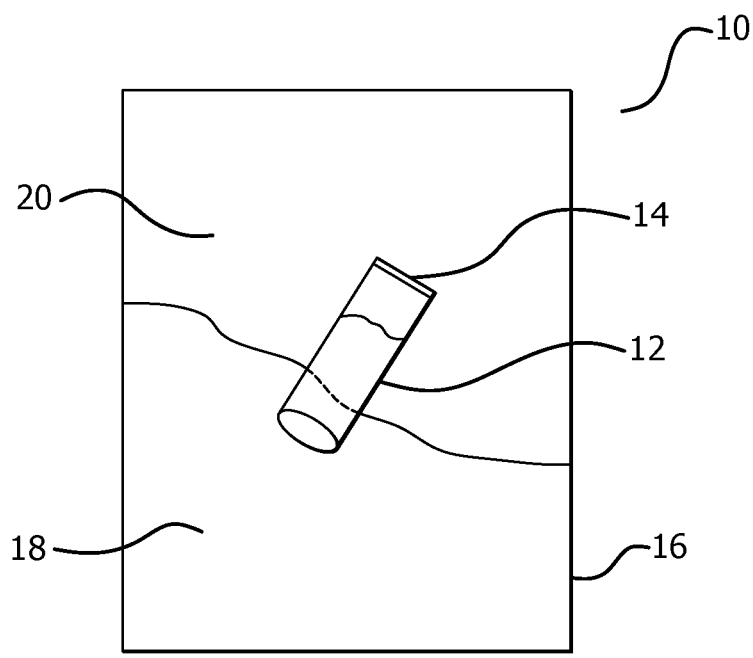
FIG. 1 shows an exemplary embodiment of a package according to the present development.

An exemplary embodiment of the present invention is shown in FIG. 1 where a package system 10 of the present invention includes a primary package or container 12 for containing and sterilizing an adhesive, a multi-layer foil seal 14 to seal container 12, and a secondary or outer package 16 that contains sealed container 12.

Container 12 is made of a cyclic olefin copolymer (COC). COCs have excellent gas and moisture barrier properties. As such, container 12 side walls include copolymers of at least one unsaturated cyclic monomer and at least one unsaturated linear monomer. Exemplary unsaturated cyclic monomers include, without limitation, cyclopentadiene and derivatives thereof such as, for example, dicyclopentadiene and 2,3-dihydrocyclopentadiene; 5,5-dimethyl-2-norbornene, 5-butyl-2-norbornene, 5-ethylidene-2-norbornene, norbornene and derivatives thereof 2-norbornene, 5-methyl-2-norbornene, 5-methoxycarbonyl-2-norbornene, 5-cyano-2-norbornene, 5-methyl-5-methoxycarbonyl-2-norbornene, and 5-phenyl-2-norbornene, and combinations of two or more thereof. Exemplary unsaturated linear monomers include, without limitation, alpha-olefins (alkenes) having from 1 to 20 carbon atoms, preferably from 1 to 12 carbon atoms, and most preferably from 1 to 6 carbon atoms. Exemplary alpha-olefins include ethylene, propylene, and butylene. Other unsaturated linear monomers may be chosen from 1-butene, 4-methyl-1-pentene, 1-hexene, 1-octene, 1-decene, 1-dodecene, 1-tetradecene, 1-hexadecene, 1-octadecene, and 1-eicocene, cydopentene, cydohexane, 3-ethylcyclohexene, cyclooctene, 1,4-hexadiene, 4-methyl-1,4-hexadiene, 5-methyl-1,4-hexadiene, 1,7-octadiene, dicyclopentadiene, 5-ethylidene-2-norbornene, 5-vinyl-2-norbornene, tetracyclododecene, 2-methyltetracyclododecene, and 2-ethyltetracyclododecene; or combinations of two or more thereof. Preferably the unsaturated linear monomer is 1-hexene, butylene, propylene, and ethylene. Preferably the copolymer is cyclopentadiene-ethylene copolymer, cyclopentadiene-butylene copolymer, cyclopentadiene-hexene copolymer, cyclopentadiene-propylene copolymer, cyclopentadiene-octene copolymer, dicyclopentadiene-ethylene copolymer, dicyclopentadiene-butylene copolymer, dicyclopentadiene-hexene copolymer, dicyclopentadiene-propylene copolymer, dicyclopentadiene-octene copolymer, norbornene-ethylene copolymer, norbornene-propylene copolymer, norbornene-butylene copolymer, norborene-hexene copolymer, 5-cyano-2-norbornene-ethylene copolymer, 5-cyano-2-norbornene-propylene copolymer, 5-cyano-2-norbornene-butylene copolymer, 5-phenyl-2-norbornene-ethylene copolymer, 5-phenyl-2-norbornene-propylene copolymer, 5-phenyl-2-norbornene-butylene copolymer, 5-methyl-5-methoxycarbonyl-2-norbornene-ethylene copolymer, 5-methyl-5-methoxycarbonyl-2-norbornene-propylene copolymer, 5-methyl-5-methoxycarbonyl-2-norbornene-butylene copolymer, 5-ethylidene-2-norbornene-ethylene copolymer, 5-ethylidene-2-norbornene-propylene copolymer, and 5-ethylidene-2-norbornene-butylene copolymer.

According to embodiments of the present invention, container 12 has a thickness between approximately 400 µm to approximately 5000 µm, preferably approximately 400 µm to approximately 4000 µm and more preferably approximately 400 µm to approximately 3000 µm. Preferably, the thickness of container 12 is at least 400 µm for the purpose of this invention.

Container 12 may be of any suitable size, shape, design, or configuration known in the art. For example, container 12 may have a volume up to about 30 mL. More specifically, container 12 may have a volume of about 0.1 mL to 30 mL, about 0.1 mL to 20 mL, about 0.1 mL to 15 mL, about 0.1 mL to 10 mL, or about 0.1 mL to 5 mL. Container 12 may be constructed as a bottle, an applicator, a vial, an ampoule, and the like. Container 12 may include, for example, a liquid containing area and a feed channel in fluid communication with the liquid containing area. Although an ampoule is exemplified herein, the ampoule may be replaced with any other suitable primary package design.

Figure 2:
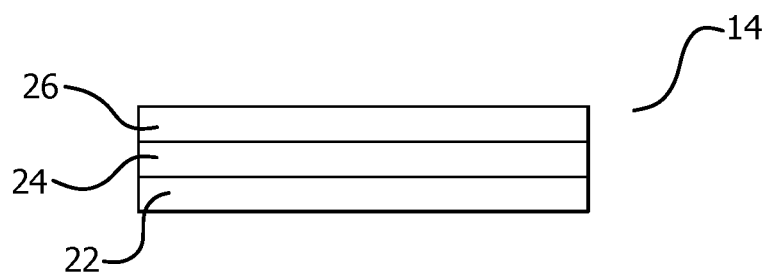
FIG. 2 shows an exemplary embodiment of a multilayer foil seal 14 shown in FIG. 1.

Once filled with adhesive, container 12 is sealed with multi-layer foil seal 14. Referring to FIG. 2, multi-layer foil seal 14 typically consists of an inner layer 22, at least one middle layer 24, and an outer layer 26. Preferably, at least inner layer 22 comprises a COC, examples of which are listed above. Examples of multilayer foil seal 14 that are suitable for use in this invention include, without limitation, from innermost layer 22 to outermost layer 26: acrylonitrile-methyl acrylate copolymer/ethylene acrylic acid copolymer/aluminum; acrylonitrile-methyl acrylate copolymer/aluminum/polypropylene; acrylonitrile-methyl acrylate copolymer/aluminum; acrylonitrile-methyl acrylate copolymer/polypropylene/aluminum; acrylonitrile-methyl acrylate/polyethylene/aluminum; acrylonitrile-methyl acrylate copolymer/ethylene acrylic acid copolymer/aluminum; acrylonitrile-methyl acrylate copolymer/aluminum/ethylene acrylic acid copolymer; acrylonitrile-methyl acrylate copolymer/aluminum/polyethylene; acrylonitrile-methyl acrylate copolymer/aluminum/polyethylene terephthalate; acrylonitrile-methyl acrylate copolymer/aluminum/polystyrene; ethylene-vinyl acetate copolymer/aluminum/polypropylene; ethylene-vinyl acetate copolymer/aluminum; ethylene-vinyl acetate copolymer/aluminum/polyethylene; ethylene-vinyl acetate copolymer/aluminum/polyethylene terephthalate; ethylene-vinyl acetate copolymer/aluminum/polystyrene; acrylonitrile-methyl acrylate copolymer/aluminum/polyethylene/polyethylene terephthalate; acrylonitrile-methyl acrylate copolymer/aluminum/polypropylene/polyethylene terephthalate; ethylene-alkyl acrylate-acrylic acid terpolymer/aluminum/polypropylene; ethylene-alkyl acrylate-acrylic acid terpolymer/aluminum; ethylene-alkyl acrylate-acrylic acid terpolymer/aluminum/polyethylene; ethylene-alkyl acrylate-acrylic acid terpolymer/aluminum/polyethylene terephthalate; ethylene-alkyl acrylate-acrylic acid terpolymer/aluminum/polystyrene, ethylene-vinyl acetate copolymer/polyethylene/polypropylene; ethylene-vinyl acetate copolymer/polystyrene/polyethylene; acrylonitrile-methyl acrylate copolymer/polypropylene/polyethylene; acrylonitrile-methyl acrylate copolymer/polyethylene/polypropylene; acrylonitrile-methyl acrylate copolymer/polysterene/polyethylene; acrylonitrile-methyl acrylate copolymer/polysterene/polypropylene; ethylene-vinyl acetate copolymer/polyvinylchloride/polypropylene; ethylene-vinyl acetate copolymer/polyvinylchloride/polyethylene; acrylonitrile-methyl acrylate copolymer/polyvinylchloride/polyethylene; polyacrylonitrile/polyvinylchloride/polypropylene; ethylene-alkyl acrylate-acrylic acid terpolymer/polypropylene/polyethylene; ethylene-alkyl acrylate-acrylic acid terpolymer/polyethylene/polypropylene; ethylene-alkyl acrylate-acrylic acid terpolymer/polystyrene/polyethylene; and ethylene-alkyl acrylate-acrylic acid terpolymer/polysterene/polyethylene.

In some embodiments, the multilayer foil seal 14 may include zero, one, two, three, four, five, six, seven, or more middle layers; and one, two, three, four, five, six, seven, or more outer layers.

The outer layer and middle layer(s) may be attached to each other by adhesives.

The middle layer and the outer layer of multilayer foil seal 14 may each independently have a thickness between about 5 μm to about 200 μm, preferably about 5 μm to 150 μm, and more preferably about 5 μm to about 100 μm. The middle and outer layers of the seal foil may independently have a thickness of about 5 μm to about 90 μm, 5 μm to about 80 μm, 5 μm to about 70 μm, about 5 μm to about 60 μm, about 10 μm to about 100 μm, about 10 μm to about 80 μm, about 10 μm to about 60 μm, about 10 μm to about 40 μm, about 20 μm to about 100 μm, about 20 μm to about 80 μm, about 20 μm to about 60 μm, or about 20 μm to about 50 μm. Although certain preferred thicknesses are described, those skilled in the art will appreciate that the thickness may be chosen so as to provide a consumer durable item that maintains structural integrity while also permitting some degree of package body flexing so as to permit dispensing of the contents.

Examples of multilayer seal foil layers suitable for use in this invention include without limitation, from outermost layer to innermost layer: polyethylene/aluminum/cyclopentadiene-ethylene copolymer; polyethylene terephthalate/polyethylene/aluminum/cyclopentadiene-ethylene copolymer; polyethylene terephthalate/polyethylene/aluminum/adhesive/cyclopentadiene-ethylene copolymer; polyethylene/aluminum/cyclopentadiene-propylene copolymer; polyethylene/aluminum/cyclopentadiene-propylene copolymer; polyethylene terephthalate/polyethylene/aluminum/cyclopentadiene-propylene copolymer; polyethylene terephthalate/polyethylene/aluminum/adhesive/cyclopentadiene-propylene copolymer; polyethylene/aluminum/cyclopentadiene-butylene copolymer; polyethylene terephthalate/polyethylene/aluminum/cyclopentadiene-butylene copolymer; polyethylene terephthalate/polyethylene/aluminum/adhesive/cyclopentadiene-butylene copolymer; polyethylene/aluminum/cyclopentadiene-hexene copolymer; polyethylene terephthalate/polyethylene/aluminum/cyclopentadiene-hexene copolymer; polyethylene terephthalate/polyethylene/aluminum/adhesive/cyclopentadiene-hexene copolymer; polyethylene/aluminum/cyclopentadiene-hexene copolymer; polyethylene terephthalate/polyethylene/aluminum/cyclopentadiene-hexene copolymer; polyethylene terephthalate/polyethylene/aluminum/adhesive/cyclopentadiene-hexene copolymer; polyethylene/aluminum/cyclopentadiene-octene copolymer; polyethylene terephthalate/polyethylene/aluminum/cyclopentadiene-octene copolymer; polyethylene terephthalate/polyethylene/aluminum/adhesive/cyclopentadiene-octene copolymer; polyethylene/aluminum/norbornene-ethylene copolymer; polyethylene terephthalate/polyethylene/aluminum/norbornene-ethylene copolymer; polyethylene terephthalate/polyethylene/aluminum/adhesive/norbornene-ethylene copolymer polyethylene/aluminum/norbornene-propylene copolymer; polyethylene/aluminum/norbornene-propylene copolymer; polyethylene terephthalate/polyethylene/aluminum/norbornene-propylene copolymer; polyethylene terephthalate/polyethylene/aluminum/adhesive/norbornene-propylene copolymer; polyethylene/aluminum/norbornene-butylene copolymer; polyethylene terephthalate/polyethylene/aluminum/norbornene-butylene copolymer; polyethylene terephthalate/polyethylene/aluminum/adhesive/norbornene-butylene copolymer; polyethylene/aluminum/norbornene-hexene copolymer; polyethylene terephthalate/polyethylene/aluminum/norbornene-hexene copolymer; polyethylene terephthalate/polyethylene/aluminum/adhesive/norbornene-hexene copolymer; polyethylene/aluminum/norbornene-hexene copolymer; polyethylene terephthalate/polyethylene/aluminum/norbornene-hexene copolymer; polyethylene terephthalate/polyethylene/aluminum/adhesive/norbornene-hexene copolymer; polyethylene/aluminum/norbornene-octene copolymer; polyethylene terephthalate/polyethylene/aluminum/norbornene-octene copolymer; polyethylene terephthalate/polyethylene/aluminum/adhesive/norbornene-octene copolymer; polyethylene/aluminum/dicyclopentadiene-ethylene copolymer; polyethylene terephthalate/polyethylene/aluminum/dicyclopentadiene-ethylene copolymer; polyethylene terephthalate/polyethylene/aluminum/adhesive/dicyclopentadiene-ethylene copolymer; polyethylene/aluminum/dicyclopentadiene-propylene copolymer; polyethylene/aluminum/dicyclopentadiene-propylene copolymer; polyethylene terephthalate/polyethylene/aluminum/dicyclopentadiene-propylene copolymer; polyethylene terephthalate/polyethylene/aluminum/adhesive/dicyclopentadiene-propylene copolymer; polyethylene/aluminum/dicyclopentadiene-butylene copolymer; polyethylene terephthalate/polyethylene/aluminum/dicyclopentadiene-butylene copolymer; polyethylene terephthalate/polyethylene/aluminum/adhesive/dicyclopentadiene-butylene copolymer; polyethylene/aluminum/dicyclopentadiene-hexene copolymer; polyethylene terephthalate/polyethylene/aluminum/dicyclopentadiene-hexene copolymer; polyethylene terephthalate/polyethylene/aluminum/adhesive/dicyclopentadiene-hexene copolymer; polyethylene/aluminum/dicyclopentadiene-hexene copolymer; polyethylene terephthalate/polyethylene/aluminum/dicyclopentadiene-hexene copolymer; polyethylene terephthalate/polyethylene/aluminum/adhesive/dicyclopentadiene-hexene copolymer; polyethylene/aluminum/dicyclopentadiene-octene copolymer; polyethylene terephthalate/polyethylene/aluminum/dicyclopentadiene-octene copolymer; polyethylene terephthalate/polyethylene/aluminum/adhesive/dicyclopentadiene-octene copolymer; polyethylene/aluminum/5-cyano-2-norbornene-ethylene copolymer; polyethylene terephthalate/polyethylene/aluminum/5-cyano-2-norbornene-ethylene copolymer; polyethylene terephthalate/polyethylene/aluminum/adhesive/5-cyano-2-norbornene-ethylene copolymer polyethylene/aluminum/5-cyano-2-norbornene-propylene copolymer; polyethylene/aluminum/5-cyano-2-norbornene-propylene copolymer; polyethylene terephthalate/polyethylene/aluminum/5-cyano-2-norbornene-propylene copolymer; polyethylene terephthalate/polyethylene/aluminum/adhesive/5-cyano-2-norbornene-propylene copolymer; polyethylene/aluminum/5-cyano-2-norbornene-butylene copolymer; polyethylene terephthalate/polyethylene/aluminum/5-cyano-2-norbornene-butylene copolymer; polyethylene terephthalate/polyethylene/aluminum/adhesive/5-cyano-2-norbornene-butylene copolymer; polyethylene/aluminum/5-cyano-2-norbornene-hexene copolymer; polyethylene terephthalate/polyethylene/aluminum/5-cyano-2-norbornene-hexene copolymer; polyethylene terephthalate/polyethylene/aluminum/adhesive/5-cyano-2-norbornene-hexene copolymer; polyethylene/aluminum/5-cyano-2-norbornene-hexene copolymer; polyethylene terephthalate/polyethylene/aluminum/5-cyano-2-norbornene-hexene copolymer; polyethylene terephthalate/polyethylene/aluminum/adhesive/5-cyano-2- norbornene-hexene copolymer; polyethylene/aluminum/5-cyano-2-norbornene-octene copolymer; polyethylene terephthalate/polyethylene/aluminum/5-cyano-2-norbornene-octene copolymer; polyethylene terephthalate/polyethylene/aluminum/adhesive/5-cyano-2-norbornene-octene copolymer; polyethylene/aluminum/5-cyano-2-norbornene-ethylene copolymer; polyethylene terephthalate/polyethylene/aluminum/5-cyano-2-norbornene-ethylene copolymer; polyethylene terephthalate/polyethylene/aluminum/adhesive/5-cyano-2-norbornene-ethylene copolymer polyethylene/aluminum/5-cyano-2-norbornene-propylene copolymer; polyethylene/aluminum/5-cyano-2-norbornene-propylene copolymer; polyethylene terephthalate/polyethylene/aluminum/5-cyano-2-norbornene-propylene copolymer; polyethylene terephthalate/polyethylene/aluminum/adhesive/5-cyano-2-norbornene-propylene copolymer; polyethylene/aluminum/5-cyano-2-norbornene-butylene copolymer; polyethylene terephthalate/polyethylene/aluminum/5-cyano-2-norbornene-butylene copolymer; polyethylene terephthalate/polyethylene/aluminum/adhesive/5-cyano-2-norbornene-butylene copolymer; polyethylene/aluminum/5-cyano-2-norbornene-hexene copolymer; polyethylene terephthalate/polyethylene/aluminum/5-cyano-2-norbornene-hexene copolymer; polyethylene terephthalate/polyethylene/aluminum/adhesive/5-cyano-2-norbornene-hexene copolymer; polyethylene/aluminum/5-cyano-2-norbornene-hexene copolymer; polyethylene terephthalate/polyethylene/aluminum/5-cyano-2-norbornene-hexene copolymer; polyethylene terephthalate/polyethylene/aluminum/adhesive/5-cyano-2-norbornene-hexene copolymer; polyethylene/aluminum/5-cyano-2-norbornene-octene copolymer; polyethylene terephthalate/polyethylene/aluminum/5-cyano-2-norbornene-octene copolymer; polyethylene terephthalate/polyethylene/aluminum/adhesive/5-cyano-2-norbornene-octene copolymer; polyethylene/aluminum/5-methyl-5-methoxycarbonyl-2-norbornene-ethylene copolymer; polyethylene terephthalate/polyethylene/aluminum/5-methyl-5-methoxycarbonyl-2-norbornene-ethylenecopolymer; polyethylene terephthalate/polyethylene/aluminum/adhesive/5-methyl-5-methoxycarbonyl-2-norbornene-ethylene copolymer polyethylene/aluminum/5-methyl-5-methoxycarbonyl-2-norbornene-propylene copolymer; polyethylene/aluminum/5-methyl-5-methoxycarbonyl-2-norbornene-propylene copolymer; polyethylene terephthalate/polyethylene/aluminum/5-methyl-5-methoxycarbonyl-2-norbornene-propylene copolymer; polyethylene terephthalate/polyethylene/aluminum/adhesive/5-methyl-5-methoxycarbonyl-2-norbornene-propylene copolymer; polyethylene/aluminum/5-methyl-5-methoxycarbonyl-2-norbornene-butylene copolymer; polyethylene terephthalate/polyethylene/aluminum/5-methyl-5-methoxycarbonyl-2-norbornene-butylene copolymer; polyethylene terephthalate/polyethylene/aluminum/adhesive/5-methyl-5-methoxycarbonyl-2-norbornene-butylene copolymer; polyethylene/aluminum/5-methyl-5-methoxycarbonyl-2-norbornene-hexene copolymer; polyethylene terephthalate/polyethylene/aluminum/5-methyl-5-methoxycarbonyl-2-norbornene-hexene copolymer; polyethylene terephthalate/polyethylene/aluminum/adhesive/5-methyl-5-methoxycarbonyl-2-norbornene-hexene copolymer; polyethylene/aluminum/5-methyl-5-methoxycarbonyl-2-norbornene-hexene copolymer; polyethylene terephthalate/polyethylene/aluminum/5-methyl-5-methoxycarbonyl-2-norbornene-hexene copolymer; polyethylene terephthalate/polyethylene/aluminum/adhesive/5-methyl-5-methoxycarbonyl-2-norbornene-hexene copolymer; polyethylene/aluminum/5-methyl-5-methoxycarbonyl-2-norbornene-octene copolymer; polyethylene terephthalate/polyethylene/aluminum/5-methyl-5-methoxycarbonyl-2-norbornene-octene copolymer; polyethylene terephthalate/polyethylene/aluminum/adhesive/5-methyl-5-methoxycarbonyl-2-norbornene-octene copolymer; polypropylene/aluminum/cyclopentadiene-ethylene copolymer; polyethylene terephthalate/polypropylene/aluminum/cyclopentadiene-ethylene copolymer; polyethylene terephthalate/polypropylene/aluminum/adhesive/cyclopentadiene-ethylene copolymer; polypropylene/aluminum/cyclopentadiene-propylene copolymer; polypropylene/aluminum/cyclopentadiene-propylene copolymer; polyethylene terephthalate/polypropylene/aluminum/cyclopentadiene-propylene copolymer; polyethylene terephthalate/polypropylene/aluminum/adhesive/cyclopentadiene-propylene copolymer; polypropylene/aluminum/cyclopentadiene-butylene copolymer; polyethylene terephthalate/polybutylene/aluminum/cyclopentadiene-butylene copolymer; polyethylene terephthalate/polybutylene/aluminum/adhesive/cyclopentadiene-butylene copolymer; polybutylene/aluminum/cyclopentadiene-hexene copolymer; polyethylene terephthalate/polybutylene/aluminum/cyclopentadiene-hexene copolymer; polyethylene terephthalate/polybutylene/aluminum/adhesive/cyclopentadiene-hexene copolymer; polybutylene/aluminum/cyclopentadiene-hexene copolymer; polyethylene terephthalate/polybutylene/aluminum/cyclopentadiene-hexene copolymer; polyethylene terephthalate/polybutylene/aluminum/adhesive/cyclopentadiene-hexene copolymer; polybutylene/aluminum/cyclopentadiene-octene copolymer; polyethylene terephthalate/polybutylene/aluminum/cyclopentadiene-octene copolymer; polyethylene terephthalate/polybutylene/aluminum/adhesive/cyclopentadiene-octene copolymer; polypropylene/aluminum/norbornene-ethylene copolymer; polyethylene terephthalate/polypropylene/aluminum/norbornene-ethylene copolymer; polyethylene terephthalate/polypropylene/aluminum/adhesive/norbornene-ethylene copolymer polypropylene/aluminum/norbornene-propylene copolymer; polypropylene/aluminum/norbornene-propylene copolymer; polyethylene terephthalate/polypropylene/aluminum/norbornene-propylene copolymer; polyethylene terephthalate/polypropylene/aluminum/adhesive/norbornene-propylene copolymer; polypropylene/aluminum/norbornene-butylene copolymer; polyethylene terephthalate/polypropylene/aluminum/norbornene-butylene copolymer; polyethylene terephthalate/polypropylene/aluminum/adhesive/norbornene-butylene copolymer; polypropylene/aluminum/norbornene-hexene copolymer; polyethylene terephthalate/polypropylene/aluminum/norbornene-hexene copolymer; polyethylene terephthalate/polypropylene/aluminum/adhesive/norbornene-hexene copolymer; polypropylene/aluminum/norbornene-hexene copolymer; polyethylene terephthalate/polybutylene/aluminum/norbornene-hexene copolymer; polyethylene terephthalate/polybutylene/aluminum/adhesive/norbornene-hexene copolymer; polybutylene/aluminum/norbornene-octene copolymer; polyethylene terephthalate/polybutylene/aluminum/norbornene-octene copolymer; polyethylene terephthalate/polybutylene/aluminum/adhesive/norbornene-octene copolymer; polypropylene/aluminum/dicyclopentadiene-ethylene copolymer; polyethylene terephthalate/polypropylene/aluminum/dicyclopentadiene-ethylene copolymer; polyethylene terephthalate/polypropylene/aluminum/adhesive/dicyclopentadiene-ethylene copolymer; polypropylene/aluminum/dicyclopentadiene-propylene copolymer; polypropylene/aluminum/dicyclopentadiene-propylene copolymer; polyethylene terephthalate/polypropylene/aluminum/dicyclopentadiene-propylene copolymer; polyethylene terephthalate/polypropylene/aluminum/adhesive/dicyclopentadiene-propylene copolymer; polypropylene/aluminum/dicyclopentadiene-butylene copolymer; polyethylene terephthalate/polypropylene/aluminum/dicyclopentadiene-butylene copolymer; polyethylene terephthalate/polypropylene/aluminum/adhesive/dicyclopentadiene-butylene copolymer; polypropylene/aluminum/dicyclopentadiene-hexene copolymer; polyethylene terephthalate/polypropylene/aluminum/dicyclopentadiene-hexene copolymer; polyethylene terephthalate/polypropylene/aluminum/adhesive/dicyclopentadiene-hexene copolymer; polypropylene/aluminum/dicyclopentadiene-hexene copolymer; polyethylene terephthalate/polypropylene/aluminum/dicyclopentadiene-hexene copolymer; polyethylene terephthalate/polybutylene/aluminum/adhesive/dicyclopentadiene-hexene copolymer; polybutylene/aluminum/dicyclopentadiene-octene copolymer; polyethylene terephthalate/polybutylene/aluminum/dicyclopentadiene-octene copolymer; polyethylene terephthalate/polybutylene/aluminum/adhesive/dicyclopentadiene-octene copolymer; polybutylene/aluminum/5-cyano-2-norbornene-ethylene copolymer; polyethylene terephthalate/polybutylene/aluminum/5-cyano-2-norbornene-ethylene copolymer; polyethylene terephthalate/polybutylene/aluminum/adhesive/5-cyano-2-norbornene-ethylene copolymer polypropylene/aluminum/5-cyano-2-norbornene-propylene copolymer; polypropylene/aluminum/5-cyano-2-norbornene-propylene copolymer; polyethylene terephthalate/polypropylene/aluminum/5-cyano-2-norbornene-propylene copolymer; polyethylene terephthalate/polypropylene/aluminum/adhesive/5-cyano-2-norbornene-propylene copolymer; polypropylene/aluminum/5-cyano-2-norbornene-butylene copolymer; polyethylene terephthalate/polypropylene/aluminum/5-cyano-2-norbornene-butylene copolymer; polyethylene terephthalate/polypropylene/aluminum/adhesive/5-cyano-2-norbornene-butylene copolymer; polypropylene/aluminum/5-cyano-2-norbornene-hexene copolymer; polyethylene terephthalate/polypropylene/aluminum/5-cyano-2-norbornene-hexene copolymer; polyethylene terephthalate/polypropylene/aluminum/adhesive/5-cyano-2-norbornene-hexene copolymer; polypropylene/aluminum/5-cyano-2-norbornene-hexene copolymer; polyethylene terephthalate/polypropylene/aluminum/5-cyano-2-norbornene-hexene copolymer; polyethylene terephthalate/polypropylene/aluminum/adhesive/5-cyano-2-norbornene-hexene copolymer; polypropylene/aluminum/5-cyano-2-norbornene-octene copolymer; polyethylene terephthalate/polypropylene/aluminum/5-cyano-2-norbornene-octene copolymer; polyethylene terephthalate/polypropylene/aluminum/adhesive/5-cyano-2-norbornene-octene copolymer; polypropylene/aluminum/5-cyano-2-norbornene-ethylene copolymer; polyethylene terephthalate/polypropylene/aluminum/5-cyano-2-norbornene-ethylene copolymer; polyethylene terephthalate/polypropylene/aluminum/adhesive/5-cyano-2-norbornene-ethylene copolymer polypropylene/aluminum/5-cyano-2-norbornene-propylene copolymer; polypropylene/aluminum/5-cyano-2-norbornene-propylene copolymer; polyethylene terephthalate/polypropylene/aluminum/5-cyano-2-norbornene-propylene copolymer; polyethylene terephthalate/polypropylene/aluminum/adhesive/5-cyano-2-norbornene-propylene copolymer; polypropylene/aluminum/5-cyano-2-norbornene-butylene copolymer; polyethylene terephthalate/polypropylene/aluminum/5-cyano-2-norbornene-butylene copolymer; polyethylene terephthalate/polypropylene/aluminum/adhesive/5-cyano-2-norbornene-butylene copolymer; polypropylene/aluminum/5-cyano-2-norbornene-hexene copolymer; polyethylene terephthalate/polybutylene/aluminum/5-cyano-2-norbornene-hexene copolymer; polyethylene terephthalate/polybutylene/aluminum/adhesive/5-cyano-2-norbornene-hexene copolymer; polybutylene/aluminum/5-cyano-2-norbornene-hexene copolymer; polyethylene terephthalate/polybutylene/aluminum/5-cyano-2-norbornene-hexene copolymer; polyethylene terephthalate/polybutylene/aluminum/adhesive/5-cyano-2-norbornene-hexene copolymer; polybutylene/aluminum/5-cyano-2-norbornene-octene copolymer; polyethylene terephthalate/polybutylene/aluminum/5-cyano-2-norbornene-octene copolymer; polyethylene terephthalate/polybutylene/aluminum/adhesive/5-cyano-2-norbornene-octene copolymer; polypropylene/aluminum/5-methyl-5-methoxycarbonyl-2-norbornene-ethylene copolymer; polyethylene terephthalate/polypropylene/aluminum/5-methyl-5-methoxycarbonyl-2-norbornene-ethylene copolymer; polyethylene terephthalate/polypropylene/aluminum/adhesive/5-methyl-5-methoxycarbonyl-2-norbornene-ethylene copolymer; polypropylene/aluminum/5-methyl-5-methoxycarbonyl-2-norbornene-propylene copolymer; polypropylene/aluminum/5-methyl-5-methoxycarbonyl-2-norbornene-propylene copolymer; polyethylene terephthalate/polypropylene/aluminum/5-methyl-5-methoxycarbonyl-2-norbornene-propylene copolymer; polyethylene terephthalate/polypropylene/aluminum/adhesive/5-methyl-5-methoxycarbonyl-2-norbornene-propylene copolymer; polypropylene/aluminum/5-methyl-5-methoxycarbonyl-2-norbornene-butylene copolymer; polyethylene terephthalate/polypropylene/aluminum/5-methyl-5-methoxycarbonyl-2-norbornene-butylene copolymer; polyethylene terephthalate/polypropylene/ aluminum/adhesive/5-methyl-5-methoxycarbonyl-2-norbornene-butylene copolymer; polypropylene/aluminum/5-methyl-5-methoxycarbonyl-2-norbornene-hexene copolymer; polyethylene terephthalate/polypropylene/aluminum/5-methyl-5-methoxycarbonyl-2-norbornene-hexene copolymer; polyethylene terephthalate/polypropylene/aluminum/adhesive/5-methyl-5-methoxycarbonyl-2-norbornene-hexene copolymer; polypropylene/aluminum/5-methyl-5-methoxycarbonyl-2-norbornene-hexene copolymer; polyethylene terephthalate/ polypropylene/aluminum/5-methyl-5-methoxycarbonyl-2-norbornene-hexene copolymer; polyethylene terephthalate/polypropylene/ aluminum/adhesive/5-methyl-5-methoxycarbonyl-2-norbornene-hexene copolymer; polybutylene/aluminum/5-methyl-5-methoxycarbonyl-2-norbornene-octene copolymer; polyethylene terephthalate/polybutylene/aluminum/5-methyl-5-methoxycarbonyl-2-norbornene-octene copolymer; polyethylene terephthalate/polybutylene/aluminum/adhesive/5-methyl-5-methoxycarbonyl-2-norbornene-octene copolymer.

In some aspects, the multilayer foil seal 14 is frangible. In some aspects, the connection between the foil seal 14 and sidewalls of container 12 is frangible. Thus, upon compromising the seal, the cyanoacrylate composition housed within the chamber may flow out from the chamber, for example, for purposes of dispensing the adhesive onto a surface to be adhered. In some aspects, the sidewalls of the ampoule/container are sufficiently flexible such that upon sufficient pressure, for example, by squeezing the sidewalls of the ampoule between the fingers of a user, the pressure within the ampoule compromises the foil seal or the connection between the foil seal and ampoule sidewalls such that the monomer composition may be released from the chamber. In some aspects, the sidewalls of the ampoule are hard but the ampoule seal is frangible. The ampoule can be connected to the applicator tip through a sleeve. One or more cutting members on the sleeve can break the seal. The cyanoacrylate composition in the ampoule may flow through the passageway in the sleeve onto the applicator tip. Flow of the adhesive composition can be controlled by squeezing the sidewalls of the sleeve.

Container 12 is typically heat-sealed with the multilayer foil seal 14 after the adhesive is filled into the container. To provide a leak-free seal, certain temperature and pressure are applied. According to embodiments of the present invention, the temperature used to seal the plastic container and the seal foil is typically in the range of from about 100° C. to about 200° C., preferably from about 100° C. to about 180° C., and more preferably from about 110° C. to about 170° C. The pressure used to seal the plastic container and the seal foil is typically in the range of from about 1 bar to about 50 bar, preferably from about 1 bar to about 40 bar, and more preferably from about 1 bar to about 15 bar. If the sealing temperature and/or pressure are too low, the seal between the plastic container and the foil seal will not be tight enough to provide a leak free container for storing and sterilizing cyanoacrylate adhesive. On the other hand, if the sealing temperature and/or pressure are too high, the plastic container can be deformed or the multilayer foil seal 14 can be damaged during the assembly process.

According to embodiments of the present invention, container 12 (i.e., the primary container for the cyanoacrylate composition) is advantageously sterilized by an irradiation method as is described in greater detail below. After the irradiation sterilization, the primary container with cyanoacrylate composition disclosed herein may be further assembled into an applicator body with the attached applicator tip for dispensing cyanoacrylate adhesive composition.

Referring again to FIG. 1, the package 10 includes a secondary package 16. Secondary package 16 preferably consists of a front wrapper 18 and a back wrapper 20. The material for front wrapper 18 may include polyethylene (PE) polytetrafluoroethylene (PFTE); polyethylene terephthalate (PET); amorphous polyethylene terephthalate (APET), polystyrene (PS), polycarbonate (PC); polypropylene (PP); polystyrene (PS); polyvinylchloride (PVC); a thermoplastic elastomer (TPE); and mixtures thereof. Front wrapper 18 preferably has a thickness of between approximately 100 μm to approximately 1000 μm, preferably approximately 200 μm to approximately 800 μm and more preferably approximately 300 μm to approximately 600 μm.

According to some embodiments of the present invention, part or entire of the secondary package 16 is made at least in part of material that is gas permeable. In certain embodiments of the current invention, back wrapper 20 is gas permeable, which is suitable for gaseous chemical sterilization such as, for example, ethylene oxide (ETO) sterilization. The material used for the back wrapper 20 includes without limitation, ultra low density of polyethylene, a medical grade Kraft paper coated with a low density polyethylene, low density nylon, cellophanelpolyethylene laminate, phenoxy, and mylarlpolyethylene laminate. Back wrapper 20 typically has a thickness of between approximately 20 μm to approximately 200 μm, preferably approximately 30 μm to approximately 150 μm, and more preferably approximately 50 μm to approximately 100 μm. Back wrapper 20 is preferably medical grade paper coated with heat sealant.

The front wrapper 18 and back wrapper 20 of the secondary package 16 preferably are heat-sealed together under elevated temperature and pressure. According to embodiments of the present invention, the temperature used to seal the front wrapper and back wrapper of the overpack is in the range of about 110° C. to about 250° C., preferably about 110° C. to about 200° C., and more preferably about 120° C. to about 180° C. The pressure used to seal the front wrapper and the back wrapper is in the range of about 1 NM (Newton Meter) to about 40 NM, preferably about 1 NM to about 30 NM, and more preferably about 1 NM to about 20 NM.

The preferred adhesive to add to container 12 is a cyanoacrylate monomer composition. Thus, the package system 10 fully assembled includes a stabilized cyanoacrylate monomer composition having a viscosity that is housed by container 12 which, in turn, is housed by secondary package 14. Container 12, which houses the stabilized cyanoacrylate monomer composition, can be sterilized by irradiation while substantially maintaining the viscosity of the composition such that the composition does not experience a significant increase in viscosity following irradiation sterilization. The secondary package 14 housing the adhesive in container 12 can be sterilized by chemical sterilization, while substantially maintaining the viscosity of the stable cyanoacrylate composition such that the composition does not experience a significant increase in viscosity following sterilization. Thus, the package system 10 provides a twice sterilized and stable cyanoacrylate composition that has a shelf life of at least 12 months, preferably at least 24 months.

The cyanoacrylate monomers may comprise any cyanoacrylate monomers or their mixtures suitable in the art for adhesive applications, particularly for medical adhesive applications. More specifically, the cyanoacrylate monomer may be an aliphatic cyanoacrylate ester and preferably an alkyl, cycloalkyl, alkenyl, alkoxyalkyl, fluroalkyl, fluorocyclic alkyl or fluoroalkoxy cyanoacrylate ester. The alkyl group may contain from 2 to 12 carbon atoms, is preferably a $C_2$ to $C_{10}$ alkyl ester, and is most preferably a $C_4$ to $C_8$ alkyl ester. Suitable cyanoacrylate esters include without limitation, the ethyl, n-propyl, iso-propyl, n-butyl, pentyl, hexyl, cyclohexyl, heptyl, n-octyl, 2-ethylhexyl, 2-methoxyethyl and 2-ethoxyethyl esters. Any of these cyanoacrylate monomers may be used alone, in combination, or they may be used as mixtures. 2-octyl cyanoacrylate monomer, as well as 2-octyl cyanoacrylate monomer mixed together with n-butyl cyanoacrylate monomer are preferred for the compositions.

The cyanoacrylate monomers may be synthesized by following procedures known in the art, for example, as described in U.S. Pat. Nos. 4,364,876, 2,721,858 and U.S. Pat. No. 3,254,111. For example, the cyanoacrylates may be prepared by reacting cyanoacetate with formaldehyde in the presence of a basic condensation catalyst at a high temperature to give a low molecular weight polymer. A depolymerization step followed under a high temperature and a high vacuum in the presence of acidic and anionic inhibitors, yields a crude monomer that can be distilled under the high vacuum in the presence of radical and acidic inhibitors. The cyanoacrylate compositions are stable in that the compositions do not deteriorate, degrade, polymerize, react, form by-products, or otherwise break down or change the properties of the composition.

The purity of cyanoacrylate may be at least about 97% by weight, preferably at least about 98% by weight, and more preferably at least about 99% by weight. The purity of cyanoacrylate monomer may be obtained through one or more processes known in the art. In an exemplary embodiment, the high purity cyanoacrylate monomers may be obtained through a distillation process. For example, the high purity of cyanoacrylate monomer may be obtained by multiple distillations under high vacuum and high temperature. The vacuum for distilling cyanoacrylate monomer may be in the range of about 0.02 Torr to about 15 Torr, preferably in the range of about 0.05 Torr to about 10 Torr, and more preferably in the range of about 0.1 Torr to about 10 Torr. The distillation temperature may be in the range of about 100° C. to about 180° C., preferably in the range of about 100° C. to about 160° C., and more preferably in the range of about 100° C. to about 150° C. The distilled cyanoacrylate monomers may be formulated with free radical and acidic inhibitors depending upon their application and stability.

Basic polymers or copolymers may be applied to reduce the amount of contaminants and extraneous additives in the cyanoacrylate monomer, but this can lead to several problems including premature polymerization. Some basic polymers or copolymers are not soluble in cyanoacrylate but are mixed with the monomer adhesive in mutual contact until the adhesive is destabilized. In order to achieve the mutual contact, such polymers or copolymers are mixed with the cyanoacrylate monomer under vacuum for a minimum of 3 hours, which may remove possible acid residues to destabilize the adhesive. The solid powder of such polymer is then removed from cyanoacrylate adhesive by filtering, for example, through a 0.2 µm filter.

Cyanoacrylate compositions can be filtered through one or multiple filters in order to reduce the bioburden level of the cyanoacrylate composition and remove any immiscible impurities or contaminants. If filtered, the cyanoacrylate monomers may be filtered through any suitable sized filters known in the art. For example, in a multiple step filtration process, the cyanoacrylate monomers may be filtered through a primary filter and one or more additional or secondary filters. The size of the primary filter may range, for example, on the order of about 0.01 to about 0.8 µm, preferably in the range of about 0.01 to about 0.6 µm, and more preferably in the range of about 0.03 to about 0.6 µm. The size of the additional or secondary filters may range, for example, on the order of about 1 to about 200 µm, preferably in the range of about 1 to about 150 µm, and more preferably in the range of about 1 to about 100 µm.

Various additives can be mixed together with the cyanoacrylate monomers as part of the cyanoacrylate compositions. Fox example, stabilizers or polymerization inhibitors can be included in order to ensure an acceptable shelf life of cyanoacrylate adhesives. Polymerization accelerators can be incorporated into cyanoacrylate compositions for improving the curing speed of the adhesives, or in other words, additives for accelerating the polymerization reaction. The adverse effect of sterilization on cyanoacrylate compositions can be exacerbated, however, in the presence of polymerization accelerators. The invention provides for a desired method for sterilizing and storing cyanoacrylate compositions in the absence or presence of a polymerization accelerator.

The cyanoacrylate monomer compositions may contain one or more stabilizers or inhibitors including free radical stabilizers, anionic stabilizers, acidic stabilizers, mixtures thereof, and other suitable stabilizers, which preferably are mixed together with the cyanoacrylate monomers. The cyanoacrylate compositions may contain one or more free radical stabilizers. Free radical stabilizers may include without limitation, hydroquinone; catechol; butylated hydroxyl anisole (BHA). hydroquinone monomethyl ether and hindered phenols, such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4methoxyphenol; 2,2methylene-bis-(4-methyl-6-tert-butylphenol); and mixtures thereof. BHA is preferred.

The free radical stabilizer, if present, may be used in an amount less than about 40,000 ppm, less than about 30,000 ppm, less than about 25,000 ppm, less than about 20,000 ppm, less than about 15,000 ppm, less than about 10,000 ppm, less than about 5000 ppm, less than about 1000 ppm, or less than about 500 ppm. For example, the amount of free radical stabilizer may range from about 200 ppm to about 30,000 ppm, about 1000 ppm to about 30,000 ppm, about 2000 ppm to about 25,000 ppm, about 3000 ppm to about 20,000 ppm, and about 3000 ppm to about 15,000 ppm.

The cyanoacrylate compositions may contain one or more anionic inhibitors or stabilizers, which may be in addition to the free radical stabilizer. Such anionic inhibitors may include without limitation sulfur dioxide, nitrogen oxide, boron oxide, phosphoric acid, ortho, meta, or para-phosphoric acid, acetic acid, benzoic acid, cyanoacetic acid, tri-fluoroacetic acid, tribromoacetic acid, trichloroacetic acid, boron trifluoride, hydrogen fluoride, perchloric acid, hydrochloric acid, hydrobromic acid, sulfonic acid, fluorosulfonic acid, chlorosulfonic acid, sulfuric acid, toluenesulfonic acid, and mixtures thereof. Sulfur dioxide is preferred.

The anionic stabilizer, if present, may be used in an amount of about 50 ppm or less, about 40 ppm or less, about 30 ppm or less, about 25 ppm or less, or about 20 ppm or less. For example, the acid stabilizer may be present in an amount of about 1 ppm to about 50 ppm, about 2 ppm to about 50 ppm, about 5 ppm to about 50 ppm, about 5 ppm to about 20 ppm, about 5 ppm to about 19 ppm, about 10 ppm to about 50 ppm, about 2 ppm to about 40 ppm, about 5 ppm to about 30 ppm, about 10 ppm to about 25 ppm, about 10 ppm to about 15 ppm, about 10 ppm to about 25 ppm, about 10 ppm to about 20 ppm, about 10 ppm to about 19 ppm, about 15 ppm to about 30 ppm, about 15 ppm to about 25 ppm, about 15 ppm to about 20 ppm, about 17 ppm to about 20 ppm, about 17 ppm to about 19 ppm, about 18 ppm to about 30 ppm, about 18 ppm to about 25 ppm, about 12 ppm to about 20 ppm, or about 13 ppm to about 19 ppm.

Viscosity includes the resistance of a fluid to flow due to a shearing force. The viscosity may be dependent upon the conditions under which it is measured, such as fluid temperature. Unless indicated otherwise, the absolute viscosity may be determined at room temperature and is expressed in units of centipoise (cPs).

The stabilized cyanoacrylate monomer compositions, which may include one or more of a polymerization accelerator, a thickening agent, or a plasticizing agent, among any other additives described or exemplified herein, comprise an initial viscosity. This initial viscosity is the viscosity of the composition with all of its constituents mixed together, without being sterilized. The initial viscosity may be less than about 400 cPs, less than about 300 cPs, less than about 200 cPs, less than about 100 cPs, less than about 50 cPs, less than about 25 cPs, less than about 20 cPs, less than about 15 cPs, less than about 10 cPs, or less than about 7 cPs. In particular, the initial viscosity of the cyanoacrylate composition may be in the range of about 3 cPs to about 100 cPs, about 3 cPs to about 50 cPs, about 3 cPs to about 20 cPs, about 3 cPs to about 10 cPs, about 4 cPs to about 15 cPs, about 4 cPs to about 8 cPs, about 5 cPs to about 10 cPs, about 5 cPs to about 7 cPs, about 5 cPs to about 9 cPs, about 5 cPs to about 8 cPs, about 5 cPs to about 100 cPs, about 5 cPs to about 50 cPs, about 5 cPs to about 20 cPs, about 5 cPs to about 15 cPs, about 10 cPs to about 20 cPs, about 10 cPs to about 25 cPs, about 6 cPs to about 7 cPs, about 6 cPs to about 8 cPs, about 6 cPs to about 10 cPs, about 7 cPs to about 10 cPs, about 7 cPs to about 9 cPs, about 10 cPs to about 50 cPs, about 10 cPs to about 20 cPs, about 15 cPs to about 20 cPs, about 15 cPs to about 25 cPs, about 10 cPs to about 30 cPs, about 20 cPs to about 25 cPs, about 20 cPs to about 30 cPs, about 25 cPs to about 50 cPs, or about 25 cPs to about 75 cPs, prior to sterilization. Cyanoacrylate compositions containing a thickening agent and/or polymerization accelerator may have higher viscosities than compositions with only a thickening agent or a polymerization accelerator or compositions with neither a thickening agent or polymerization accelerator.

Large amounts of stabilizer can increase the toxicity of the cyanoacrylate compositions. The cyanoacrylate compositions with small amounts of stabilizer packaged as described in the invention provide for long term stability of the cyanoacrylate formulations. For example, the desirable barrier property of the package system may work in concert to provide the stability of the cyanoacrylate compositions in the presence of such small amounts of stabilizer. It is thus an advantage of the invention to provide safe, stabilized cyanoacrylate compositions in the package systems.

Compared to cyanoacrylate compositions generally known in the art, the cyanoacrylate compositions stored in the package body of the invention contain much smaller amounts of anionic stabilizer, such as sulfur dioxide, if present at all. For example, U.S. Pat. No. 5,480,935 provides for cyanoacrylate adhesive compositions with high amounts of sulfur dioxide as the anionic stabilizer, for example, on the order of about 150 to 250 ppm. U.S. Pat. No. 5,730,994 and U.S. Pat. No. 5,807,563 provide for about 50 to 500 ppm sulfur dioxide as the anionic polymerization inhibitor. In the examples of U.S. Publ. No. 2006/0062687, 100 ppm of sulfur dioxide was used to stabilize cyanoacrylate compositions.

The cyanoacrylate composition may include one or more dyes or colorants. In particular, the dyes may include derivatives of anthracene and other complex structures. Examples of suitable dyes include, but are not limited to, 1-hydroxy-4-[4-methylphenylamino]-9,10 anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); and 2-(1,3dihydro-3-oxo-5-sulfo-2H-indole-2-ylidine)-2,3-dihydro-3-oxo- 1H-ind-ole-5 sulfonic acid disodium salt (FD&C Blue No. 2), and the like. If present, small amounts of the dye may be used. For example, the cyanoacrylate composition may include one or more dyes in an amount of 1000 ppm or less, 500 ppm or less, 250 ppm or less, 100 ppm or less, or 50 ppm or less. For example, the dye may be present in an amount of about 1 ppm to about 1000 ppm, about 5 ppm to about 500 ppm, about 5 ppm to about 250 ppm, or about 5 ppm to about 100 ppm.

The cyanoacrylate composition may include one or more plasticizers or plasticizing agents. The plasticizing agent preferably does not contain any moisture and should not adversely affect the stability of the cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl) phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG), and mixtures thereof. Tributyl citrate, diisodecyl adipate and acetyl tributyl citrate may be preferred. The plasticizer, if present, is in an amount based on weight % of the cyanoacrylate composition of 20% or less, 15% or less, 10% or less, 7.5% or less, 5% or less, 2.5% or less or 1% or less.

The cyanoacrylate composition may include one or more thickeners or thickening agents. Suitable thickening agents may include, but are not limited to, polycyanoacrylate, partial polymer of cyanoacrylate, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, triblock copolymers of polyoxypropylene flanked by two hydrophilic chains of polyoxyethylene, and mixtures thereof. Preferred thickening agents, if present, can be a partial polymer of cyanoacrylate as described in U.S. Pat. No. 8,198,344. Preferred thickening agents can also be triblock copolymers of polyoxyalkylene as described in U.S. Pat. No. 8,293,838. Preferably the thickening agent is miscible in the cyanoacrylate monomer compositions at room temperature. Biocompatible thickening agents are preferred for use in the medical field.

The amount of thickening agent, if present, may be present in an amount less than about 8000 ppm, less than about 7000 ppm, less than about 6000 ppm, less than about 5000 ppm. The amount of thickening agent may range, for example from about 10 ppm to about 8000 ppm, about 40 ppm to about 8000 ppm, about 60 ppm to about 7000 ppm, or about 100 ppm to about 6000 of the liquid adhesive composition.

The cyanoacrylate composition may include one or more polymerization accelerators, preferably mixed together with the cyanoacrylate monomers. Suitable polymerization accelerators may be selected from, without limitation, calixarenes and oxacalixarenes, silacrowns, crown-ethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, polyalkylene oxides and derivatives, and mixtures thereof.

In a preferred embodiment, a crown ether is used as the polymerization accelerator. Examples of crown ethers include, but are not limited to, 15-crown-5, 18-crown-6, dibenzo-18-crown-6, tribenzo-18-crown-6, dicyclohexyl-18-crown-6, benzo-15-crown5, dibenzo-24-crown- 8, dibenzo-30-crown- 10, asym-dibenzo-22-crown-6, dimethylsila- 11-crown-4, dimethylsila-14-crown-5, dimethylsila-17-crown-6, dibenzo-14-crown-4, dicyclohexyl24-crown-8, asym-dibenzo-22-crown-6, cyclohexyl-12-crown-4, 1,2-decalyl-15-crown-5, 1,2naphtho-15-crown-5, 3,4,5-naphthyl-16-crown-5, 1,2-methyl-benzo-18-crown-6, 1,2methyl-benzo-5 ,6-methylbenzo- 18-crown-6, 1,2-t-butyl-18-crown-6, 1,2-vinylbenzo-15-crown-5, 1,2-vinylbenzo-18-crown-6, 1,2-t-butyl-cyclohexyl-18-crown-6, and 1,2-benzo-1,4-benzo-5oxygen-20-crown-7. The crown ether is preferably mixed together with the cyanoacrylate monomer.

The polymerization accelerator may be present in an amount less than about 6000 ppm, less than about 5000 ppm, less than about 4000 ppm, less than about 3000 ppm, less than about 2000 ppm, less than about 1000 ppm, less than about 750 ppm, less than about 500 ppm, less than about 250 ppm, less than about 100 ppm, or less than about 50 ppm. The amount of polymerization accelerator may range, for example from about 10 ppm to about 6000 ppm, about 10 ppm to about 2000 ppm, about 10 ppm to about 1200 ppm, about 10 ppm to about 1100 ppm, about 10 ppm to about 1000 ppm, about 20 ppm to about 2000 ppm, about 20 ppm to about 1500 ppm, about 20 ppm to about 1000 ppm, about 30 ppm to about 4000 ppm, about 30 ppm to about 3000 ppm, about 30 ppm to about 2000 ppm, about 30 ppm to about 1200 ppm, about 30 ppm to about 1000 ppm, about 40 ppm to about 1500 ppm, about 40 ppm to about 1200 ppm, about 40 ppm to about 1100 ppm, about 40 ppm to about 1000 ppm, about 50 ppm to about 3000 ppm, about 50 ppm to about 2000 ppm, about 50 ppm to about 1500 ppm, about 50 ppm to about 1200 ppm, about 50 ppm to about 1100 ppm, about 50 ppm to about 1000 ppm, about 75 ppm to about 1500 ppm, about 75 ppm to about 1000 ppm, about 100 ppm to about 5000 ppm, about 100 ppm to about 4000 ppm, about 100 ppm to about 3000 ppm, about 100 ppm to about 2000 ppm, about 100 ppm to about 1500 ppm, about 100 ppm to about 1300 ppm, about 100 ppm to about 1200 ppm, about 100 ppm to about 1100 ppm, about 100 to about 1000 ppm, about 250 ppm to about 1250 ppm, about 250 ppm to about 1100 ppm, about 300 ppm to about 2000 ppm, about 300 ppm to about 1200 ppm, about 300 ppm to about 1100 ppm, about 500 ppm to about 1200 ppm, about 500 ppm to about 1100 ppm, about 500 ppm to about 1000 ppm, or about 60 ppm to about 1200 ppm of the adhesive composition.

With the presence of a polymerization accelerator, the setting time of the cyanoacrylate composition upon irradiation sterilization may be in the range of about 5 to about 120 seconds, preferably about 10 to 90 seconds, and more preferably about 10 to about 60 seconds.

The primary package or ampoule or container contains the stable cyanoacrylate composition or adhesive. In other words, the ampoule or container has a chamber, and this chamber is filled with the stabilized cyanoacrylate monomer composition. The chamber or container preferably includes an opening through which the composition may be inserted in order to fill the chamber. The opening of the chamber is then closed by sealing it with a foil seal. The foil seal may be frangible.

The present invention provides for a desired method for sterilizing and storing cyanoacrylate compositions in the absence or presence of a polymerization accelerator. The method for sterilizing cyanoacrylate compositions in a desired package system comprising the COC container 12 includes (1) preparing cyanoacrylate monomer with a purity of about 98% by weight; (2) stabilizing cyanoacrylate compositions with free radical and anionic polymerization inhibitors and dissolving polymerization accelerator in cyanoacrylate compositions; (3) filling cyanoacrylate compositions into a primary package; (4) sterilizing cyanoacrylate compositions in the primary package system via irradiation method; (5) assembling the primary package into the applicator with the applicator tip and packing into a secondary overpack; and (6) sterilizing the whole package system via a chemical sterilization. Compared to the sterilization of cyanoacrylate compositions disclosed in prior arts, the method disclosed in the current invention is advantageous. First of all, the method disclosed herein provides a desired method of sterilizing cyanoacrylate compositions with a miscible polymerization accelerator in direct contact during the sterilization. On the contrast, prior arts teach that a non-contacting relationship between the polymerization accelerator and the adhesive composition has to be maintained during the sterilization process and prior to the application in order to prevent the potential pre-mature polymerization of the adhesive induced by the sterilization, as seen in U.S. Pat. Nos. 6,579,469 to Nicholson et al; 6,620,846 to Jonn et al.; and 5,928,611 to Leung, as well as in U.S. Pat. Appl. Pub. Nos. 2005/0047846 to Narang et al.; 2007/0078207 to Jonn et al.; 2010/0330027 to Liu, 2010/0269749 to Badejo et al., and 2008/0241249 to Quintero et al. In addition, the method of sterilizing cyanoacrylate composition in said package systems disclosed herein provides sterile cyanoacrylate composition an extended shelf life of at least 24 months. Last but not the least, the method of sterilizing cyanoacrylate composition in said package system can offset the potential side effect of irradiation sterilization on other parts of the package system such as the applicator body that holds the primary container, the applicator tip for dispensing the adhesive, and the secondary overpack. It is known that irradiations have various effects on different package materials made of polymers, copolymers or other components, such as changing color, affecting tensile properties, and oxidizing of the package material upon irradiation. In particular, irradiation can turn most of polymer-based white packaging materials into yellow, which makes the package components such as the applicator body, the applicator tip and the secondary overpack cosmetically and aesthetically undesirable or unacceptable. The method of sterilizing cyanoacrylate composition disclosed herein only exposes the primary container for the adhesive composition to irradiation, while the rest of the components of the package system are sterilized by a chemical sterilization, which can effectively inhibit the side effect of irradiation on the packaging materials.

The primary container or ampoule containing the cyanoacrylate monomer composition is sterilized. Preferably, the primary container or ampoule containing the cyanoacrylate composition is sterilized by an irradiation method. In particular, the cyanoacrylate adhesive compositions in the primary package may be sterilized by Gamma, X-ray, Microwave, E-beam sterilization, or a combination thereof. Although these sterilization methods are described in detail herein, the sterilization may also comprise some combination of each of these irradiation techniques. The primary package (ampoule or container) is compatible with various irradiation methods for storing and sterilizing cyanoacrylate adhesive compositions. The package materials are stable under the desired dosage of the irradiation sterilization, and do not degrade as a result of the exposure to the radiation. The primary package provides a desired barrier to moisture so that it is compatible with the cyanoacrylate monomer compositions.

In one embodiment, the primary container and cyanoacrylate composition contained therein is sterilized with gamma irradiation. The dose of gamma irradiation applied to the package containing cyanoacrylate compositions should be sufficient enough to sterilize both the package and the adhesive inside. The dose of gamma irradiation may range, for example, from about 5 to about 25 kGy, about 5 to about 20 kGy, about 5 to about 15 kGy, or about 5 to about 10 kGy. Standard Cobalt Co-60 may be used as the gamma ray source in sterilizing the compositions and packages of the invention.

In another embodiment, the primary container and cyanoacrylate composition contained therein is sterilized with X-ray irradiation. The dose of X-ray irradiation applied to the package containing cyanoacrylate compositions should also be sufficient enough to sterilize both the package and the adhesive inside. The dose of X-ray irradiation to cyanoacrylate compositions contained in the packages may range, for example, from about 5 kGy to about 40 kGy, about 5 kGy to about 30 kGy, about 5 kGy to about 25 kGy, or about 5 kGy to about 20 kGy. High energy electrons are preferably used for the X-ray sterilization of the liquid adhesive compositions. X-rays are generated as high-frequency and short-wavelength electromagnetic photons. Conventional X-ray technology may be suitable. The X-ray energy used to sterilize the primary container and the cyanoacrylate composition may range from about 1 million to about 10 million electron volts (MeV), about 3 MeV to 10 MeV, or about 3 to 7.5 MeV.

In another embodiment, the primary container and cyanoacrylate composition contained therein is sterilized with E-beam irradiation. The dose of E-beam irradiation applied to the package containing cyanoacrylate compositions should be sufficient enough to sterilize both the package and the adhesive inside. The E-beam irradiation can be in a suitable dosage amount, for example, of from about 5 to 50 kGy, and more preferably from about 12 to 25 kGy. E-beam irradiation may be conducted at any suitable temperature and pressure known in the art. Preferably, the E-beam irradiation may be conducted at ambient atmosphere conditions and the exposure time to the irradiation may be within 60 seconds, for example.

The absorbed dosage is specific to the type of the product and its density, the beam power, beam energy, scan height, and the speed at which the products moves through the electron beam. The power source for the electrons of E-beam irradiation is the linear accelerator, which is measured in kilo watts (KW). The larger the beam power is, the more product volume can be processed. The cyanoacrylate adhesive compositions stored in the primary packages may be irradiated at a beam power ranging from about 2 KW to about 30 KW, preferably about 5 KW to about 20 KW, and more preferably about 10 KW to about 20 KW.

E-beam irradiation for the cyanoacrylate compositions stored in the primary package involves the use of high-energy electrons. The beam energy may range from 1 million to 10 million electron volts (MeV), preferably 3 MeV to 10 MeV, and more preferably 5 to 10 MeV. The elevated energy levels are required to penetrate cyanoacrylate adhesive compositions, which are sterilized in the primary package or ampoule.

The processing speed also affects the delivered dosage of E-beam to the cyanoacrylate compositions stored in the primary packages. The processing speed may be controlled by the process conveyer that conveys the product through the beam at a given speed. The processing speed may range from about 1 to 20 feet per minute (fpm), preferably from about 2 to 15 fpm, and more preferably from about 4 to 10 fpm. The scan height of the E-beam may be in the range of about 16 inches to 30 inches, preferably in the range of about 20 to 30 inches, and more preferably in the range of about 25 to 30 inches.

Before or after the irradiation sterilization, the primary container or ampoule containing the cyanoacrylate composition may be further assembled into an applicator body. For example, the applicator body may have an attached applicator tip for dispensing the cyanoacrylate adhesive composition. The applicator may include a reservoir container and a sponge application tip, for example. The sponge tip may be saturated with liquid adhesive once it is folded over so that adhesive can be dispensed uniformly onto the wound site. In order to inhibit premature polymerization, the volume of the applicator is preferably about 50 to 80 percent and more preferably 60 to 80 percent filled by the cyanoacrylate adhesives. The cyanoacrylate adhesive compositions in the packages such as, for example, an applicator with an overpack can be sterilized by E-beam, Gamma, or X-ray irradiation in different configurations.

With respect to the viscosity of the cyanoacrylate composition, it will be appreciated by those skilled in the art that the viscosity of cyanoacrylate adhesive compositions generally increases following irradiation. It is preferred, however, that in accordance with the storage container of the invention, the viscosity does not change dramatically, either higher or lower, during or subsequent to the irradiation process.

After irradiation sterilization in the primary package, the viscosity of the cyanoacrylate composition may change, including an increase or decrease to a second viscosity. The change in viscosity of the cyanoacrylate adhesive compositions, after the sterilization, may vary, for example, depending on the original viscosity and the presence of additives such as a polymerization accelerator or thickening agent. When stored in the primary package, however, the change in viscosity is preferably minimal. Preferably, the viscosity of the composition after sterilization (in the primary package/ampoule) is within about 1% to about 100% of the initial viscosity of the composition, before sterilization. In some embodiments, the viscosity of the composition after sterilization is within about 5% to about 300% of the initial viscosity of the composition, before sterilization. The viscosity may change about 5% to about 10%, about 5% to about 15%, about 5% to about 20%, about 7% to about 10%, about 7% to about 15%, about 8% to about 12%, about 8% to about 15%, about 8% to about 20%, about 10% to about 100%, about 10% to about 80%, about 10% to about 60%, about 10% to about 40%, about 10% to about 30%, about 10% to about 20%, about 20% to about 100%, about 20% to about 60%, about 20% to about 50%, about 20% to about 40%, about 20% to about 30%, about 30% to about 300%, about 30% to about 200%, about 30% to about 150%, about 30% to about 100%, about 30% to about 50%, about 40% to about 300%, about 40% to about 200%, about 40% to about 150%, about 40% to about 100%, about 40% to about 80%, about 40% to about 80%, about 50% to about 300%, about 50% to about 200%, about 50% to about 150%, about 50% to about 100%, about 50% to about 90%, about 50% to about 80%, about 60% to about 200%, about 60% to about 100%, about 70% to about 200%, about 70% to about 100%, about 80% to about 100% of the initial viscosity.

This second viscosity, the viscosity of the composition in the ampoule/container after irradiation sterilization, but before the second sterilization step, may be less than about 400 cPs, less than about 300 cPs, less than about 200 cPs, less than about 100 cPs, less than about 50 cPs, less than about 25 cPs, less than about 20 cPs, less than about 15 cPs, less than about 10cPs, or less than about 7 cPs. In particular, the second viscosity of the cyanoacrylate composition may be in the range of about 3 cPs to about 100 cPs, about 3 cPs to about 50 cPs, about 3 cPs to about 20 cPs, about 3 cPs to about 10 cPs, about 4 cPs to about 15 cPs, about 5 cPs to about 10 cPs, about 5 cPs to about 7 cPs, about 5 cPs to about 9 cPs, about 5 cPs to about 8 cPs, about 5 cPs to about 100 cPs, about 5 cPs to about 50 cPs, about 5 cPs to about 20 cPs, about 5 cPs to about 15 cPs, about 10 cPs to about 20 cPs, about 10 cPs to about 25 cPs, about 6 cPs to about 7 cPs, about 6 cPs to about 8 cPs, about 6 cPs to about 10 cPs, about 6 cPs to about 14 cPs, about 7 cPs to about 12 cPs, about 7 cPs to about 10 cPs, about 10 cPs to about 60 cPs, about 10 cPs to about 15 cPs, about 15 cPs to about 20 cPs, about 15 cPs to about 25 cPs, about 15 cPs to about 30 cPs, about 10 cPs to about 15 cPs, about 10 cPs to about 20 cPs, about 20 cPs to about 25 cPs, about 20 cPs to about 30 cPs, about 25 cPs to about 50 cPs, about 25 cPs to about 75 cPs, or about 25 cPs to about 30 cPs, prior to the second sterilization.

Generally speaking, after the cyanoacrylate composition contained within the primary package or ampoule is sterilized by irradiation, the viscosity of the cyanoacrylate formulation is substantially the same as the initial viscosity (pre-irradiation). In particular, the primary package or ampoule is sterilized by irradiation while maintaining the viscosity of the stable cyanoacrylate composition such that a change in the viscosity is no more than a small amount. In some aspects, the change between the initial viscosity of the cyanoacrylate composition and the second viscosity of the cyanoacrylate composition after irradiation sterilization is preferably less than about 30 cPs, less than about 25 cPs, less than about 22 cPs, less than about 20 cPs, less than about 19 cPs, less than about 18 cPs, less than about 17 cPs, less than about 16 cPs, less than about 15 cPs, less than about 14 cPs, less than about 13 cPs, less than about 12 cPs, less than about 11 cPs, less than about 10 cPs, less than about 9 cPs, less than about 8 cPs, less than about 7 cPs, less than about 6 cPs, less than about 5 cPs, less than about 4 cPs, or less than about 3 cPs.

The viscosity of the cyanoacrylate monomer compositions including the thickening agents stored in the primary package may change upon irradiation sterilization. The change of the viscosity may depend, for example, on the presence or absence of certain additives in the composition, including a thickening agent (e.g., a partial polymer of cyanoacrylate may be used as the thickening agent to prepare the cyanoacrylate compositions with a desired level of high viscosity) and/or a polymerization accelerator.

The primary package and secondary overpack can be further sterilized by chemical sterilization. The chemical sterilization method includes without limitation, ozone sterilization, ethylene oxide sterilization, hydrogen peroxide sterilization, formaldehyde sterilization, and peracetic acid sterilization. The preferred chemical sterilization for sterilizing said primary package and secondary overpack is ethylene oxide sterilization.

The invention provides for a suitable package system for cyanoacrylate compositions, which can be sterilized via irradiation sterilization while maintaining the viscosity of the cyanoacrylate composition. The primary package (ampoule or container) is made of materials which are gas/moisture resistant. The barrier property and stability upon irradiation of the primary package make it a suitable container to sterilize and store the cyanoacrylate compositions. The cyanoacrylate compositions, even in the presence of small amounts of stabilizers, can be packaged in the primary package and can be sterilized in the packaging with irradiation sterilization.

Once the adhesive container is assembled into the applicator body with the applicator tip, the primary package (containing the monomer composition) together with the secondary overpack may be further sterilized by chemical sterilization. The chemical sterilization method may include without limitation, ozone sterilization, ethylene oxide sterilization, hydrogen peroxide sterilization, formaldehyde sterilization, and peracetic acid sterilization. In an exemplary embodiment, the chemical sterilization for sterilizing the primary package containing the cyanoacrylate composition and the secondary overpack is ethylene oxide (ETO) sterilization.

When the cyanoacrylate composition contained within the primary package and also contained within the secondary overpack is sterilized a second time, the second time by chemical sterilization, the viscosity of the cyanoacrylate composition is maintained at or approximate to the viscosity of the initial viscosity and/or the second viscosity. Nevertheless, the viscosity may change following the chemical sterilization. The secondary overpack may be sterilized by chemical sterilization while substantially maintaining the second viscosity of the stable cyanoacrylate composition such that a change in the viscosity is no more than a small amount. After the second sterilization, the cyanoacrylate monomer composition has a third viscosity. Preferably, the change in viscosity from the second to the third viscosity is less than about 30 cPs, less than about 25 cPs, less than about 22 cPs, less than about 20 cPs, less than about 18 cPs, less than about 17 cPs, less than about 16 cPs, less than about 15 cPs, less than about 14 cPs, less than about 13 cPs, less than about 12 cPs, less than about 11 cPs, less than about 10 cPs, less than about 9 cPs, less than about 8 cPs, less than about 7 cPs, less than about 6 cPs, less than about 5 cPs, less than about 4 cPs, or less than about 3 cPs.

The viscosity may change from the second to the third viscosity may be about 5% to about 10%, about 5% to about 20%, about 7% to about 10%, about 8% to about 20%, about 8% to about 15%, about 10% to about 100%, about 10% to about 80%, about 10% to about 60%, about 10% to about 40%, about 10% to about 30%, about 10% to about 20%, about 20% to about 100%, about 20% to about 60%, about 20% to about 50%, about 20% to about 40%, about 20% to about 30%, about 30% to about 300%, about 30% to about 200%, about 30% to about 150%, about 30% to about 100%, about 30% to about 50%, about 30% to about 40%, about 40% to about 300%, about 40% to about 200%, about 40% to about 150%, about 40% to about 100%, about 40% to about 80%, about 40% to about 80%, about 40% to about 50%, about 50% to about 300%, about 50% to about 200%, about 50% to about 150%, about 50% to about 100%, about 50% to about 90%, about 50% to about 80%, about 60% to about 200%, about 60% to about 100%, about 70% to about 200%, about 70% to about 100%, about 80% to about 100% of the second viscosity.

This third viscosity, the viscosity of the composition in the ampoule housed in the overpack after irradiation sterilization and chemical sterilization but before simulated aging conditions (80 degrees C. for about 12 or about 13 days), may be less than about 400 cPs, less than about 300 cPs, less than about 200 cPs, less than about 100 cPs, less than about 50 cPs, less than about 25 cPs, less than about 20 cPs, less than about 15 cPs, less than about 10cPs, or less than about 7 cPs. In particular, the third viscosity of the cyanoacrylate composition may be in the range of about 3 cPs to about 100 cPs, about 3 cPs to about 50 cPs, about 3 cPs to about 20 cPs, about 3 cPs to about 12 cPs, about 4 cPs to about 15 cPs, bout 4 cPs to about 12 cPs, about 5 cPs to about 10 cPs, about 5 cPs to about 7 cPs, about 5 cPs to about 9 cPs, about 5 cPs to about 8 cPs, about 5 cPs to about 100 cPs, about 5 cPs to about 50 cPs, about 5 cPs to about 20 cPs, about 5 cPs to about 15 cPs, about 10 cPs to about 15 cPs, about 10 cPs to about 20 cPs, about 10 cPs to about 25 cPs, about 6 cPs to about 7 cPs, about 6 cPs to about 10 cPs, about 6 cPs to about 14 cPS, about 7 cPs to about 12 cPs, about 7 cPs to about 10 cPs, about 10 cPs to about 60 cPs, about 10 cPs to about 25 cPs, about 15 cPs to about 20 cPs, about 15 cPs to about 25 cPs, about 15 cPs to about 30 cPs, about 10 cPs to about 15 cPs, about 10 cPs to about 20 cPs, about 20 cPs to about 25 cPs, about 20 cPs to about 30 cPs, about 25 cPs to about 50 cPs, about 25 cPs to about 75 cPs, or about 25 cPs to about 30 cPs, prior to the advanced aging storage.

The invention provides for a suitable package system for cyanoacrylate compositions, which can be sterilized twice: first via irradiation sterilization and second via chemical sterilization, while substantially maintaining the initial viscosity of the cyanoacrylate composition throughout the entire process. The cyanoacrylate compositions, even in the presence of thickening agents and/or polymerization accelerators, can be packaged in the primary package and subsequently in the secondary overpack and can be sterilized in the packaging with chemical sterilization. The combination of the primary package with the stable cyanoacrylate compositions and the two-step sterilization provide for an extended shelf life of the cyanoacrylate compositions of at least one year, preferably at least two years.

The twice-sterilized package system, including the ampoule containing a sterilized cyanoacrylate monomer composition and the overpack, maintains stability to the cyanoacrylate composition within the package system when stored over time, particularly at normal or ambient temperature and humidity conditions attendant to shelf storage of such a package system. The stability is reflected in minimal viscosity changes in the composition over the storage time. The sterilized composition is viscosity-stable for at least two years of shelf storage. Two years of shelf storage may be simulated with a standard advanced aging test, which subjects the package system (including the composition therein) to 80 degrees C. for at least 12 days, and in some aspects 13 days.

Following the accelerated aging test, the viscosity of the composition may change from the third viscosity to a fourth viscosity. Following the accelerated aging test, the composition substantially maintains the third viscosity such that a change in the viscosity is no more than a small amount. Preferably, the change in viscosity from the second to the third viscosity is less than about 400 cPs, less than about 300 cPs, less than about 200 cPs, less than about 150 cPs, less than about 100 cPs, less than about 75 cPs, less than about 50 cPs, less than about 25 cPs, less than about 22 cPs, less than about 20 cPs, less than about 18 cPs, less than about 17 cPs, less than about 16 cPs, less than about 15 cPs, less than about 14 cPs, less than about 13 cPs, less than about 12 cPs, less than about 11 cPs, less than about 10 cPs, less than about 9 cPs, less than about 8 cPs, less than about 7 cPs, less than about 6 cPs, less than about 5 cPs, or less than about 4 cPs.

The viscosity may change from the third to the fourth viscosity may be about 5% to about 10%, about 5% to about 20%, about 7% to about 10%, about 10% to about 100%, about 10% to about 80%, about 10% to about 60%, about 10% to about 40%, about 10% to about 30%, about 10% to about 20%, about 20% to about 100%, about 20% to about 60%, about 20% to about 50%, about 20% to about 40%, about 20% to about 30%, about 30% to about 500%, about 30% to about 400%, about 30% to about 300%, about 30% to about 200%, about 30% to about 150%, about 30% to about 100%, about 30% to about 50%, about 30% to about 40%, about 40% to about 500%, about 40% to about 400%, about 40% to about 300%, about 40% to about 200%, about 40% to about 150%, about 40% to about 100%, about 40% to about 80%, about 40% to about 80%, about 40% to about 50%, about 50% to about 500%, about 50% to about 400%, about 50% to about 300%, about 50% to about 200%, about 50% to about 150%, about 50% to about 100%, about 50% to about 90%, about 50% to about 80%, about 60% to about 200%, about 60% to about 100%, about 70% to about 200%, about 70% to about 100%, about 80% to about 100%, about 100% to about 200%, about 100% to about 300%, about 100% to about 350%, about 200% to about 300%, or about 200% to about 400% of the third viscosity.

This fourth viscosity, the viscosity of the composition in the ampoule housed in the overpack after irradiation sterilization, chemical sterilization, and simulated advanced aging conditions (80 degrees C. for about 12 or about 13 days), may be less than about 400 cPs, less than about 300 cPs, less than about 200 cPs, less than about 100 cPs, less than about 50 cPs, less than about 25 cPs, less than about 20 cPs, less than about 15 cPs, less than about 10cPs, or less than about 7 cPs. In particular, the third viscosity of the cyanoacrylate composition may be in the range of about 3 cPs to about 100 cPs, about 3 cPs to about 50 cPs, about 3 cPs to about 20 cPs, about 4 cPs to about 15 cPs, about 5 cPs to about 10 cPs, about 5 cPs to about 7 cPs, about 5 cPs to about 9 cPs, about 5 cPs to about 8 cPs, about 5 cPs to about 100 cPs, about 5 cPs to about 50 cPs, about 5 cPs to about 35 cPs, about 5 cPs to about 20 cPs, about 5 cPs to about 15 cPs, about 10 cPs to about 20 cPs, about 10 cPs to about 25 cPs, about 10 cPs to about 30 cPs, about 10 cPs to about 35 cPs, about 10 cPs to about 40 cPs, about 6 cPs to about 7 cPs, about 6 cPs to about 10 cPs, about 6 cPs to about 14 cPS, about 6 cPs to about 26 cPs, about 7 cPs to about 12 cPs, about 7 cPs to about 10 cPs, about 10 cPs to about 60 cPs, about 10 cPs to about 45 cPs, about 10 cPs to about 40 cPs, about 10 cPs to about 35 cPs, about 10 cPs to about 30 cPs, about 15 cPs to about 20 cPs, about 15 cPs to about 25 cPs, about 15 cPs to about 30 cPs, about 15 cPs to about 35 cPs, about 15 cPs to about 45 cPs, about 15 cPs to about 50 cPs, about 10 cPs to about 15 cPs, about 20 cPs to about 25 cPs, about 20 cPs to about 30 cPs, about 20 cPs to about 35 cPs, about 20 cPs to about 40 cPs, about 20 cPs to about 50 cPs, about 25 cPs to about 50 cPs, about 25 cPs to about 75 cPs, about 25 cPs to about 30 cPs, about 25 cPs to about 35 cPs, about 26 cPs to about 29 cPs, or about 26 cPs to about 30 cPs.

The viscosity fourth viscosity may be about 10% to about 500% higher than the first viscosity. The fourth viscosity may be about 5% to about 50%, about 5% to about 100%, about about 10% to about 350%, about 10% to about 300%, about 10% to about 250%, about 10% to about 100%, about 30% to about 400%, about 30% to about 350%, about 30% to about 300%, about 30% to about 200%, about 30% to about 100%, about 50% to about 500%, about 50% to about 400%, about 50% to about 350%, about 50% to about 300%, about 50% to about 150%, about 70% to about 400%, about 70% to about 350%, about 70% to about 300%, about 70% to about 200%, about 100% to about 500%, about 100% to about 400%, about 100% to about 350%, about 100% to about 330%, about 100% to about 300%, about 100% to about 250%, about 150% to about 400%, about 150% to about 350%, about 150% to about 250%, about 150% to about 200%, about 200% to about 400%, about 200% to about 350%, about 200% to about 300%, about 250% to about 400%, about 250% to about 350%, about 300% to about 350%, or about 310% to about 340% of the first viscosity.

According to one embodiment, the method or process for producing and sterilizing the cyanoacrylate compositions in a package system may include: (a) inserting a stabilized cyanoacrylate composition having a desires viscosity into an ampoule such as any ampoule described or exemplified herein, (b) sealing the ampoule containing the stable cyanoacrylate composition with a foil seal, including any foil seal described or exemplified herein, (c) sterilizing the sealed ampoule containing the stabilized cyanoacrylate composition via irradiation sterilization, (d) placing the sterilized and sealed ampoule into an overpack to provide a package system, and (f) sterilizing the package system via a chemical sterilization. Optionally, the methods may include preparing a stable cyanoacrylate composition, which may optionally comprise one or more additives such as a polymerization accelerator, plasticizer, or thickener.

According to another embodiment, a method or process for producing and sterilizing the cyanoacrylate compositions in a package system may include: (a) preparing cyanoacrylate monomer with a purity of between about 97-99% by weight; (b) stabilizing the cyanoacrylate compositions with free radical and anionic polymerization inhibitors and dissolving a polymerization accelerator in the cyanoacrylate compositions; (c) filling the cyanoacrylate compositions into a primary package and sealing the primary package; (d) sterilizing the cyanoacrylate compositions in the primary package via one or more irradiation methods; (e) assembling the primary package into the applicator with the applicator tip and packing the assembled device into a secondary overpack; and (f) sterilizing the whole package system via a chemical sterilization.

This method or process provides a number of benefits, including, but not limited to: (1) allowing direct contact between the cyanoacrylate composition and an optional polymerization accelerator during the sterilization and storage; (2) superior shelf life stability; (3) inhibiting or preventing adverse side effects of irradiation on the packaging materials; and (4) producing a sterile and shelf-stable cyanoacrylate monomer composition.

The process provides for a way of sterilizing the cyanoacrylate compositions with a miscible polymerization accelerator, which is preferably mixed together with the cyanoacrylate composition during sterilization. Generally, polymerization accelerators may induce polymerization and/or make polymerization proceed rapidly such that the polymerization accelerator and the adhesive composition had to be separated during sterilization, and maintained separated until just prior to applying the composition to the materials to be adhered together in order to prevent the premature polymerization of the adhesive induced by the sterilization and facilitated by the accelerator. This is evidenced by U.S. Pat. Nos. 6,579,469, 6,620,846, and U.S. Pat. No. 5,928,611, as well as in U.S. Publ. Nos. 2005/0047846, 2007/0078207, 2010/0330027, 2010/0269749, and 2008/0241249.

Second, the stable cyanoacrylate composition along with the method of sterilizing the cyanoacrylate composition in the package system provides for sterile cyanoacrylate compositions with an extended shelf life of at least 12 months, preferably at least 15 months, more preferably at least 18 months, and even more preferably at least 24 months. Thus, the package system is capable of being stored at room temperature (e.g., about 20° C. to about 25° C.) for long periods of time without substantially increasing in viscosity, deteriorating, degrading, polymerizing, or otherwise reacting or changing in properties. The shelf life of a product may be evaluated by any suitable technique. For example, the package system may undergo an accelerated aging test at elevated temperature to evaluate the shelf life stability of the cyanoacrylate compositions. This test can be performed in an oven at 80° C. for a period of 13 days. Based on ASTM F1980-2, 13 days accelerated aging at 80° C. correlates to 2 years of shelf life at ambient temperatures. Similarly, a real time shelf life study could also be conducted. At the end of 2 years of shelf life evaluated by real time study or accelerated aging studies, cyanoacrylate compositions in the package system sterilized by irradiation method preferably have a viscosity of less than about 400 cPs, more preferably less than about 300 cPs, and most preferably less than about 200 cPs.

Third, the method of sterilizing cyanoacrylate compositions in the package system can offset the potential side effect of irradiation sterilization on other parts of the package system such as the applicator body that holds the primary container, the applicator tip for dispensing the adhesive, and the secondary overpack. It is known that irradiations have various effects on different package materials made of polymers, copolymers or other components, such as changing color, affecting tensile properties, and oxidizing of the package material upon irradiation. In particular, irradiation can turn most of polymer-based white packaging materials into yellow, which makes the package components such as the applicator body, the applicator tip and the secondary overpack cosmetically and aesthetically undesirable or unacceptable. The method of sterilizing cyanoacrylate composition disclosed herein only exposes the primary container for the adhesive composition to irradiation, while the rest components of the package system are sterilized by a chemical sterilization, which can effectively inhibit the side effect of irradiation on the packaging materials.

Fourth, a stable and sterile cyanoacrylate product may be produced. For example, a sterility assurance level (SAL) can be obtained at a minimum of $10^{-3}$, which means that the probability of a single unit being non-sterile after sterilization is 1 in 1000. In more preferred embodiments, the sterility assurance level may be at least $10^{-6}$. The sterility of the cyanoacrylate monomer composition packaged in the package system after E-beam sterilization was analyzed by Bacteriostasis and Fungistasis tests. After testing with challenging microorganisms, such as *Bacillus subtilis, Candida albicans*, and *Aspergillus niger*, no growth of the microorganisms was observed for the cyanoacrylate adhesive in the package system after E-beam sterilization, indicating the sterility of the cyanoacrylate adhesives.

The following non-limiting examples are intended to further illustrate, but not to limit, the invention.

EXAMPLE 1

Shelf Life Stability of Various Cyanoacrylate Compositions in Different Package Medium As summarized in Table 1, three formulations were considered under different irradiation techniques: (1) Formulation A: stabilized 2-octyl cyanoacrylate mixed together with a polymerization accelerator; (2) Formulation B: stabilized mixture of 2-octyl cyanoacrylate and n-butyl cyanoacrylate; (3) Formulation C: stabilized 2-octyl cyanoacrylate; and (4) Formulation D: stabilized mixture of 2-octyl cyanoacrylate and n-butyl cyanoacrylate with high concentration of colorant; and (5) Formulation E: stabilized n-butylcyanoacrylate. The formulations, respectively, were stored in a container made of cyclic olefin copolymer and multi-layer seal foil or multiple layer materials with cyclic olefin copolymer as the adhesive contacting inner layer. The ampoule container was initially sterilized by irradiation method, which may be assembled into the applicator with the applicator tip. The ampoule or the ampoule-applicator assembly was then packaged into the overpack, which was re-sterilized by a chemical sterilization. The compositions in the other comparative containers, such as polypropylene (PP), low density polyethylene (LDPE), etc. were sterilized by irradiation only.

As shown in Table 1, the cyanoacrylate compositions stored in the package system of the present invention can provide a shelf life of at least 24 months under irradiation technique such as Gamma. This was confirmed by an accelerated aging test by storing the sterilized package containing a sterilized cyanoacrylate composition at 80 degrees C. for 13 days. In comparison, however, the same cyanoacrylate adhesive compositions contained in other package systems made of only low density polyethylene (LDPE), high density polyethylene (HDPE), and polypropylene, amber HDPE, glass, and polyethylene terephthalate glycol were not found to be as stable upon irradiation sterilization. The cyanoacrylate compositions packaged in other systems as listed below were cured in about a month after the irradiation sterilization, exhibiting an unacceptable shelf life. The cyanoacrylate compositions packaged in the package system provide the extended shelf life of at least two years after irradiation sterilization. These observations demonstrate the uniqueness of the package system disclosed herein as a suitable container for the cyanoacrylate compositions.

TABLE 1

Shelf life stability of cyanoacrylate compositions in different packages under various irradiation sterilizations

| Formulation | Container Material | Irradiation | Shelf stability in container, post-irradiation sterilization |
|---|---|---|---|
| A | Clear Flint glass bottles | Gamma | Cured upon sterilization |
| A | Amber glass bottles | Gamma | Cured upon sterilization |
| A | Natural LDPE bottle | Gamma | 1575 cps (too viscous) at day 13 when stored at 80 degrees C. |
| E | Natural PP bottle | Gamma | Nearly cured at day 13 when stored at 80 degrees C. |
| E | Natural HDPE bottle | Gamma | 1382 cps (too viscous) at day 13 when stored at 80 degrees C. |
| E | Clear flint Glass | Gamma | Cured at day 13 when stored at 80 degrees C. |
| E | PETG bottle | Gamma | Nearly cured at day 13 when stored at 80 degrees C. |
| E | White LDPE bottle | Gamma | Nearly cured at day 13 when stored at 80 degrees C. |
| B | PP Applicator | Gamma | All cured at month 1 when stored at 40 degree C. |
| B | MDPE applicator | Gamma | All cured at month 1 when stored at 40 degree C. |
| B | Polypropylene* | E-beam | Cured in about a month |
| B | Low density polyethylene* | E-beam | Cured in about a month |
| A | Amber HPDE* | E-beam | Cured in about a month |
| A | Polypropylene* | E-beam | Cured in about a month |
| A | Amber glass* | E-beam | Cured in about a month |
| A | Low density polyethylene* | E-beam | Cured in about a month |

TABLE 1-continued

Shelf life stability of cyanoacrylate compositions in different packages under various irradiation sterilizations

| Formulation | Container Material | Irradiation | Shelf stability in container, post-irradiation sterilization |
|---|---|---|---|
| B | High density polyethylene* | E-beam | Cured in about a month |
| A | High density polyethylene* | E-beam | Cured in about a month |
| A | Package system of the invention | Gamma | At least 24 months |
| B | Package system of the invention | Gamma | At least 24 months |
| C | Package system of the invention | Gamma | At least 24 months |
| D | Package system of the invention | Gamma | At least 24 months |
| E | Package system of the invention | Gamma | At least 24 months |

EXAMPLE 2

Shelf Life Stability and Viscosity Measurement

The accelerated aging test at elevated temperature was also used to evaluate the shelf life stability of the cyanoacrylate compositions packaged in the primary package of the invention. The test can be performed in the oven at 80° C. for a period of 13 days. Based on ASTM F1980-2, 13 days accelerated aging at 80° C. correlates to 2 years of shelf life at ambient temperatures. The investigated compositions were tested for viscosity at different intervals of the aging process. As shown in Table 2, the viscosity of the cyanoacrylate composition in the package system after irradiation sterilization slightly increases as the accelerated aging proceeds but the increased viscosity of the aged samples at day 13 is so slight that it does not affect the performance of the cyanoacrylate composition or dispensing of the compositions from the packaging delivery system. The results demonstrate that the package systems are compatible with irradiation sterilization techniques so that cyanoacrylate compositions packaged inside can be sterilized via irradiation methods and provide long term stability of at least 2 years without adversely affecting the viscosity or performance of the cyanoacrylate compositions.

TABLE 2

The viscosity of various formulations in primary package of the invention, sterilized by irradiation at 9.9-11.3 kGy, at different intervals of the accelerated aging at 80° C.

| Formulation | Gamma sterilization dose | Viscosity (cps) | | |
|---|---|---|---|---|
| | | Day 0 | Day 6 | Day 13 |
| A | 9.9-11.3 kGy | 8.52 | 27.1 | 71.3 |
| B | 9.9-11.3 kGy | 5.53 | 10.1 | 60.8 |
| C | 9.9-11.3 kGy | 6.85 | 11.9 | 71.4 |
| D | 9.9-11.3 kGy | 4.68 | 7.09 | 59.9 |
| E | 9.2-10.8 kGy | 2.96 | 4.90 | 112.5 |

EXAMPLE 3

Setting Time Measurement

Pig skin was prepared by wiping the surfaces of the skin with sterile gauze saturated with isopropanol. All oily substances were thereby removed from the pig skin. The surface was then wiped with sterile gauze to remove the isopropanol. The applicator containing cyanoacrylate was opened and adhesive was permitted to saturate the sponge applicator tip for about 10 seconds prior to application. A thin film was applied to the pig skin after which elapsed time was recorded by a stop watch. Set time was then recorded by stopping the clock when the film was dry as determined at the point where no liquid transfer occurred when the film was touched with a gloved finger. Formulated cyanoacrylate compositions were packaged in the applicators and sterilized by Gamma sterilization at the dose range of 9.9-11.3 kGy. Table 3 shows the set time of these various cyanoacrylate compositions contained in the primary container after Gamma sterilization.

TABLE 3

Set time measurement of various cyanoacrylate formulations in the primary package of the invention after Gamma sterilization

| | Set-time (Seconds) | | |
|---|---|---|---|
| Formulation | Day 0 | Day 6 | Day 13 |
| A | 21.3 | 22.5 | 30.0 |
| B | 28.8 | 30.0 | 32.5 |
| C | 18.8 | 20.0 | 31.3 |
| D | 31.3 | 33.8 | 41.3 |

EXAMPLE 4

Sterility Test

The sterility of the cyanoacrylate compositions in the package was evaluated by the USP bacteriostasis and fungistasis test using the direct transfer method. The test samples were immersed into 500 ml of Soybean Casein Digest Medium (SCDM). The test microorganism, such as *Bacillus subtilis*, *Candida albicans*, and *Aspergillus niger*, was inoculated into each of the test sample containers and into a positive control container of the same medium at less than 100 colony forming units. All preparations were performed in an aseptic manner within a filtered clean bench. In order to obtain a quantitative measure of each microorganism, a duplicate plate count was performed. After inoculation, the test sample and positive control container were incubated at 20-25° C. for a five day maximum incubation period. Inoculated containers were observed periodically throughout the incubation period. Growth of the challenging microorganism was used to indicate the sterility. Cyanoacrylate compositions in the package system were sterilized by various irradiations and tested for sterility; no growth of the challenging microorganism was observed.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

We claim:

1. A package system suitable for sterilizing cyanoacrylate compositions, wherein the package system comprises:
   a container comprising
      a chamber containing a cyanoacrylate monomer, wherein the chamber is defined by an opening and sidewalls, wherein the container comprises a material comprising a first cyclic olefin copolymer;
   a multilayer foil seal sealing the opening of the container, the multilayer foil seal comprising
      an inner-most layer consisting of
         a second cyclic olefin copolymer consisting of a first unsaturated cyclic monomer and a first unsaturated linear monomer,
         wherein the first unsaturated cyclic monomer is selected from the group consisting of norbornene, and
         wherein the first unsaturated linear monomer is selected from the group consisting of ethylene, propylene, and tetracyclododecene,
      an outer layer, and
      at least one middle layer comprising aluminum; and
   a secondary package housing the container;
   wherein the package system is sterilized by radiation, and the cyanoacrylate monomer contained in the package system does not cure upon radiation exposure and for at least 24 months of shelf storage thereafter.

2. The package system of claim 1 wherein the first cyclic olefin copolymer is a copolymer of a second unsaturated cyclic monomer and at least one second unsaturated linear monomer.

3. The package system of claim 2 wherein the at least one second unsaturated linear monomer is an alpha-olefin having from 1 to 20 carbon atoms.

4. The package system of claim 3 wherein the second unsaturated linear monomer is an alpha-olefin having from 1 to 12 carbon atoms.

5. The package system of claim 2 wherein the first cyclic olefin copolymer is selected from the group consisting of norbornene-ethylene copolymer and norbornene-propylene copolymer.

6. The package system of claim 1 wherein the second cyclic olefin copolymer is selected from the group consisting of norbornene-ethylene copolymer and norbornene-propylene copolymer.

7. The package system of claim 1, wherein the package system is produced by a process comprising the following steps:
   (a) inserting a stabilized cyanoacrylate monomer composition into the chamber of the container;
   (b) sealing the opening of the chamber with the multilayer foil seal, thereby containing the composition within the chamber;
   (c) sterilizing the container containing the composition by irradiation;
   (d) surrounding the sterilized container with the secondary package, wherein the secondary package comprises a front wrapper and a back wrapper and sealing the front wrapper and back wrapper together to form the secondary package; and,
   (e) sterilizing the secondary package containing the container containing the composition by chemical sterilization.

8. The package system of claim 7, wherein the chemical sterilization of step (e) comprises ethylene oxide sterilization.

* * * * *